US008148151B2

(12) United States Patent
Zhao et al.

(10) Patent No.: US 8,148,151 B2
(45) Date of Patent: Apr. 3, 2012

(54) DIFFERENTIATION OF PRIMATE PLURIPOTENT CELLS TO HEPATOCYTE-LINEAGE CELLS

(75) Inventors: Debiao Zhao, Edinburgh (GB); Anish Sen Majumdar, Mumbai (IN); David C. Hay, Midlothian (GB); Wei Cui, London (GB)

(73) Assignees: Geron Corporation, Menlo Park, CA (US); The University Court of the University of Edinburgh, Edinburgh (GB)

(*) Notice: Subject to any disclaimer, the term of this patent is extended or adjusted under 35 U.S.C. 154(b) by 605 days.

(21) Appl. No.: 12/303,104

(22) PCT Filed: Jun. 1, 2007

(86) PCT No.: PCT/US2007/012982
§ 371 (c)(1),
(2), (4) Date: Apr. 17, 2009

(87) PCT Pub. No.: WO2007/143117
PCT Pub. Date: Dec. 13, 2007

(65) Prior Publication Data
US 2010/0086999 A1     Apr. 8, 2010

Related U.S. Application Data

(60) Provisional application No. 60/810,416, filed on Jun. 2, 2006.

(51) Int. Cl.
*C12N 15/02* (2006.01)
*C12N 5/071* (2010.01)
(52) U.S. Cl. .................. 435/377; 435/384; 435/370
(58) Field of Classification Search .................. None
See application file for complete search history.

(56) References Cited

U.S. PATENT DOCUMENTS

| | | | |
|---|---|---|---|
| 5,030,105 | A | 7/1991 | Kuri-Harcuch et al. |
| 5,532,156 | A | 7/1996 | Talbot et al. |
| 5,559,022 | A | 9/1996 | Naughton et al. |
| 5,576,207 | A | 11/1996 | Reid et al. |
| 5,763,255 | A | 6/1998 | Swiderek et al. |
| 5,869,243 | A | 2/1999 | Jauregui et al. |
| 6,017,760 | A | 1/2000 | Jauregui et al. |
| 6,129,911 | A | 10/2000 | Faris |
| 6,458,589 | B1 | 10/2002 | Rambhatla et al. |
| 6,506,574 | B1 | 1/2003 | Rambhatla et al. |
| 7,256,042 | B2 | 8/2007 | Carpenter et al. |
| 7,282,366 | B2 | 10/2007 | Carpenter et al. |
| 7,473,555 | B2 | 1/2009 | Mandalam et al. |
| 2002/0146678 | A1 | 10/2002 | Benvenisty |
| 2003/0138948 | A1 | 7/2003 | Fisk et al. |
| 2005/0037493 | A1 | 2/2005 | Mandalam et al. |
| 2005/0042748 | A1 | 2/2005 | Ochiya et al. |
| 2006/0003446 | A1 | 1/2006 | Keller et al. |
| 2009/0136955 | A1 | 5/2009 | Mandalam et al. |

FOREIGN PATENT DOCUMENTS

| | | |
|---|---|---|
| EP | 0 827 742 A1 | 3/1998 |
| EP | 0 827 743 A1 | 3/1998 |
| EP | 0 953 633 A1 | 11/1999 |
| WO | WO 91/15573 A1 | 10/1991 |
| WO | WO 95/12665 A1 | 5/1995 |
| WO | WO 97/47307 A1 | 12/1997 |
| WO | WO 97/47734 A1 | 12/1997 |
| WO | WO 99/23885 A1 | 5/1999 |
| WO | WO 99/37150 A1 | 7/1999 |
| WO | WO 00/03001 A1 | 1/2000 |
| WO | WO 00/18239 A1 | 4/2000 |
| WO | WO 00/22098 A1 | 4/2000 |
| WO | WO 00/43498 A2 | 7/2000 |
| WO | WO 00/50048 A2 | 8/2000 |
| WO | WO 01/39784 A1 | 6/2001 |
| WO | WO 01/49113 A1 | 7/2001 |
| WO | WO 01/62901 A2 | 8/2001 |
| WO | WO 01/81549 A2 | 11/2001 |
| WO | 2005042703 A2 | 5/2005 |
| WO | 2007002385 A2 | 1/2007 |
| WO | 2007075807 A2 | 7/2007 |

OTHER PUBLICATIONS

Chen, Y-G. et al., "Activin signalling and its role in regulation of cell proliferation, apoptosis, and carcinogenesis," Exp. Biol. Med. 231(5) (2006), pp. 534-544.
Hay, D. et al., "Efficient differentiation of hepatocytes from human embryonic stem cells exhibiting markers recapitulating liver development in vivo," Stem Cells 26(4) (2008), pp. 894-902.
Soto-Gutierrez, A. et al., "Differentiation of human embryonic stem cells to hepatocytes using deleted variant of HGF and poly-amino-urethane-coated nonwoven polytetrafluoroethylene fabric," Cell Transplantation 15(4) (2006), pp. 335-341.
Abe et al., Endoderm-Specific Gene Expression in Embryonic Stem Cells Differentiated to Embryoid Bodies, Exp. Cell Res. 229:27-34 (1996).
Hamazaki et al., Hepatic maturation in differentiating embryonic stem cells in vitro, FASEB Journal 15:A1084 (2001).
Bluethmann et al., Establishment of the role of IL-6 and TNF receptor 1 using gene knockout mice. J. Leukoc. Biol. 56:565-570; 1994.
Adams, R. et al., "Effective cryopreservation and long-term storage of primary human hepatocytes with recovery of viability, differentiation, and replicative potential," Cell Transplantation 4(6):579-86 (1995).
Agelli, M. et al., "Putative liver progenitor cells: conditions for long-term survival in culture," Histochemical J. 29:205-17 (1997).
Alberts, B. et al., *Molecular Biology of the Cell*, Garland Publishing, Inc., New York, pp. 66, 85, 347 (1989).
Alison, M., "Liver stem cells: a two compartment system," Curr. Op. Cell Biol. 10:710-15 (1998).

(Continued)

*Primary Examiner* — Deborah Crouch
(74) *Attorney, Agent, or Firm* — Law Office of Salvatore Arrigo and Scott Lee, LLP

(57) ABSTRACT

Methods for differentiating primate pluripotent stem cells into hepatocyte-lineage cells are provided. In certain embodiments, the methods utilize sequential culturing of the primate pluripotent stem cells in certain growth factors to produce hepatocyte-lineage cells. In certain embodiments, the population of cells produced by the methods is further enriched for hepatocyte-lineage cells.

22 Claims, 14 Drawing Sheets

OTHER PUBLICATIONS

ATCC website info. For Chang liver cells, ATCC # CCL-1, 7 pages (2004).
Baribault, H. & Marceau, N., "Dexamethasone and dimethylsulfoxide as distinct regulators of growth and differentiation of cultured suckling rat hepatocytes," *J. Cell Physiol.* 129(1):77-84 (1986).
Block, G. et al., "Population expansion, clonal growth, and specific differentiation patterns in primary cultures of hepatocytes induced by HGF/SF, EGF and TGFα in a chemically defined (HGM) medium," *J. Cell Biol.* 132(6):1133-49 (1996).
Blouin, M. et al., "Specialization switch in differentiating embryonic rat liver progenitor cells in response to sodium butyrate," *Exp. Cell Res.* 217:22-30 (1995).
Bodnar, A. et al., "Extension of life-span by introduction of telomerase into normal human cells," *Science* 279:349-52 (1998).
Brill, S. et al., "Expansion conditions for early hepatic progenitor cells from embryonal and neonatal rat livers," *Dig Diseases & Sci.* 44(2):364-71 (1999).
Buommino, E. et al., "Sodium butyrate/retinoic acid costimulation induces apoptosis-independent growth arrest and cell differentiation in normal and ras-transformed seminal vesicle epithelial cells unresponsive to retinoic acid," *J. Mol. Endocrinol.* 24(1):83-94 (2000).
Cai, J. et al., "Directed differentiation of human embryonic stem cells into functional hepatic cells," *Hepatol.* 45:1229-39 (2007).
Chen, H-L. et al., "Long-term culture of hepatocytes from human adults," *J. Biomed. Sci.* 5:435-40 (1998).
Chen, W. et al., "Reactivation of silenced, virally transduced genes by inhibitors of histone deacetylase," *Proc. Natl. Acad. Sci. USA* 94:5798-803 (1997).
Cherny, R. et al., "Strategies for the isolation and characterization of bovine embryonic stem cells," *Reprod. Fertil. Dev.* 6:569-75 (1994).
Chinzei, R. et al., "Embryoid-body cells derived from a mouse embryonic stem cell line show differentiation into functional hepatocytes," *Hepatol.* 36:22-29 (2002).
Choi, D. et al., "Differentiation of embryonic stem cells into hepatocytes," *Tissue Eng.* 6(6):675 Abstract O-43 (2000).
Coghlan, A., "Highly Cultured," *New Scientist* 2252:14 (Aug. 19, 2000).
Coleman, W. et al., "Development of dexamethasone-inducible tyrosine aminotransferase activity in WB-F344 rat liver epithelial stemlike cells cultured in the presence of sodium butyrate," *J. Cell Physiol.* 161(3):463-69 (1994).
Davis, M. et al., "Involvement of $G_i\alpha 2$ in sodium butyrate-induced erythroblastic differentiation of K562 cells," *Biochem. J.* 346:455-61 (2000).
Devereux, T. et al., "DNA methylation analysis of the promoter region of the human telomerase reverse transcriptase (*hTERT*) gene," *Cancer Res.* 59:6087-90 (1999).
Enat, R. et al., "Hepatocyte proliferation in vitro: Its dependence on the use of serum-free hormonally defined medium and substrata of extracellular matrix," *Proc. Natl. Acad. Sci. USA* 81:1411-15 (1984).
Engelmann, G. et al., "Effect of sodium butyrate on primary cultures of adult rat hepatocytes," *In Vitro Cell. Dev. Biol.* 23(2):86-92 (1987).
Falasca, L. et al., "The effect of retinoic acid on the re-establishment of differentiated hepatocyte phenotype in primary culture," *Cell Tissue Res.* 293:337-47 (1998).
Germain, L. et al., "Biliary epithelial and hepatocytic cell lineage relationships in embryonic rat liver as determined by the differential expression of cytokeratins, α-fetoprotein, albumin, and cell surface-exposed components" *Cancer Res.* 48:4909-18 (1988).
Germain, L. et al., "Promotion of growth and differentiation of rat ductular oval cells in primary culture," *Cancer Res.* 48(2):368-78 (1988).
Gillenwater, A. et al., "Effects of sodium butyrate on growth, differentiation, and apoptosis in head and neck squamous carcinoma cell lines," *Head Neck* 22(3):247-56 (2000).
Gladhaug, I. et al., "Effects of butyrate on epidermal growth factor receptor binding, morphology, and DNA synthesis in cultured rat hepatocytes," *Cancer Res.* 48(22):6560-64 (1988).

Graham, K. et al., "Sodium butyrate induces differentiation in breast cancer cell lines expressing the estrogen receptor," *J. Cell Physiol.* 136(1):63-71 (1988).
Granérus, M. & Engström, W., "Growth factors and apoptosis," 14:309-14 (1996).
Grisham, J. et al., "Liver stem cells," *Stem Cells* pp. 233-282 (1997).
Guixiang, T. et al., "Different effects of cyclic AMP and butyrate on eosinophilic differentiation, apoptosis and bcl-2 expression of a human eosinophilic leukemia cell line, EoL-1," *Hematol Oncol.* 14(4):181-92 (1996).
Hamazaki, T. et al., "Hepatic maturation in differentiating embryonic stem cells in vitro," *FEBS Lett.* 497(1):15-19 (2001).
Hayashi, Y. et al., "Liver enriched transcription factors and differentiation of hepatocellular carcinoma," *Meth. Pathol.* 52:19-24 (1999).
Hoshi, H. et al., "Direct analysis of growth factor requirements for isolated human fetal hepatocytes," *In Vitro Cell. Dev. Biol.* 23(10):723-32 (1987).
Imamura, T. et al., "Embryonic stem cell-derived embryoic bodies in three-dimensional culture system form hepatocyte-like cells in Vitro and in Vivo," *Tissue Eng.* 10(11/12):1716-24 (2004).
Itskovitz-Eldor, J. et al., "Differentiation of human embryonic stem cells into embryoid bodies comprising the three embryonic germ layers," *Molec. Med.* 6:88-95 (2000).
Jeng, J. et al., "Effects of butyrate and propionate on the adhesion, growth, cell cycle kinetics, and protein synthesis of cultured human gingival fibroblasts," *J. Periodontol.* 70(12):1435-42 (1999).
Kamitani, H., et al., "Regulation of 12-lipoxygenase in rat intestinal epithelial cells during differentiation and apoptosis induced by sodium butyrate," *Arch. Biochem. Biophys.* 368(1):45-55 (1999).
Kaneko, Y. et al., "Alteration of differentiation state of human hepatocytes cultured with novobiocin and butyrate," *Cancer Res.* 50:3101-5 (1990).
Kobayashi, N. et al., "Establishment of a highly differentiated immortalized human hepatocyte cell line as a source of hepatic function in the bioartificial liver," *Transplant. Proc.* 32:237-41 (2000).
Kono, Y. et al., "Extended primary culture of human hepatocytes in a collagen gel sandwich system," *In Vitro Cell. Dev. Biol.—Animal* 33:467-72 (1997).
Kosugi, H. et al., "Histone deacetylase inhibitors are the potent inducer/enhancer of differentiation in acute myeloid leukemia: a new approach to anti-leukemia therapy," *Leukemia* 13:1316-24 (1999).
Koutsovelkidis, I. et al., "Butyrate inhibits and *Escherichia coli*-derived mitogen(s) stimulate DNA synthesis in human hepatocytes in vitro," *Prep. Biochem. Biotechnol.* 29(2):121-38 (1999).
Kubo, A. et al., "Development of definitive endoderm from embryonic stem cells in culture," *Development* 131:1651-62 (2003).
Lavon, N. & Benvenisty, N., "Study of hepatocyte differentiation using embryonic stem cells," *J. Cell. Biochem.* 96:1193-1202 (2005).
Lavon, N. et al., "Differentiation and isolation of hepatic-like cells from human embryonic stem cells," *Differentiation* 72:230-8 (2004).
Lázaro, C. et al., "Generation of hepatocytes from oval cell precursors in culture," *Cancer Res.* 58:5514-22 (1998).
Lee, J-H. et al., "Histone deacetylase activity is required for embryonic stem cell differentiation," *Genesis* 38:32-8 (2004).
Li, J. et al., "Mammalian hepatocyte differentiation requires the transcription factor HNF-4α," *Genes & Dev.* 14:464-474 (2000).
Masuda et al., "Up-regulation of E-cadherin and β-catenin in human hepatocellular carcinoma cell lines by sodium butyrate and interferon-α," *In Vitro Cell. Dev. Biol. Animal* 36:387-94 (2000).
Matsui, T. & Taketo, A., "Induction of catecholamine synthesis in human neuroblastoma cells by replication inhibitors and sodium butyrate," *Brain Res.* 843:112-17 (1999).
McBain, J. et al., "Apoptotic death in adenocarcinoma cell lines induced by butyrate and other histone deacetylase inhibitors," *Biochem Pharm.* 53:1357-68 (1997).
Michalopoulos, G. et al., "Morphogenetic events in mixed cultures of rat hepatocytes and nonparenchymal cells maintained in biological matrices in the presence of hepatocyte growth factor and epidermal growth factor," *Hepatology* 29(1):90-100 (1999).
Mitaka, T. et al., "Redifferentiation of proliferated rat hepatocytes cultured in L15 medium supplemented with EGF and DMSO," *In Vitro Cell Dev. Biol.* 29A:714-722 (1993).

Mitaka, T., "The current status of primary hepatocyte culture," *Int. J. Exp. Path.* 79:393-409 (1998).
Moreadith, R. & Radford, N., "Gene targeting in embryonic stem cells: the new physiology and metabolism," *J. Mol. Med.* 75:208-16 (1997).
Niki, T. et al., "A histone deacetylase inhibitor, trichostatin A, suppresses myofibroblastic differentiation of rat hepatic stellate cells in pimary culture," *Hepatology* 29(3):858-867 (1999).
Pack, R. et al., "Isolation, biochemical characterization, long-term culture, and pheotype modulation of oval cells from carcinogen-fed rats," *Exp Cell Res.* 204(2):198-209 (1993).
Pagan, R. et al., "Effects of growth and differentiation factors on the epithelial-mesenchymal transition in cultured neonatal rat hepatocytes," *J. Hepatol.* 31:859-904 (1999).
Pease, S. et al., "Isolation of embryonic stem (ES) cells in media supplemented with recombinant leukemia inhbitory factor (LIF)," *Dev. Biol.* 141:344-52 (1990).
Pera et al., "Human embryonic stem cells," *J. Cell Sci.* 113:5-10 (2000).
Perez, R. et al., "Sodium butyrate upregulates Kupffer cell $PGE_2$ production and modulates immune function," *J. Surg. Res.* 78(1):1-6 (1998).
Perrine, S. et al., "A short-term trial of butyrate to stimulate fetal-globin-gene expression in the beta-globin disorders," *N. Engl. J. Med.* 328(2):81-86 (1993).
Perrine, S. et al., "Butyrate derivatives. New agents for stimulating fetal globin production in the β-globin disorders," *Am. J. Pediatr. Hemotol. Oncol.* 16(1):67-71 (1994).
Rambhatla, L. et al., "Generation of hepatocyte-like cells from human embryonic stem cells," *Cell Transplantation* 12:1-11 (2003).
Rathjen, P. et al., "Properties and uses of embryonic stem cells: prospects for application to human biology and gene therapy," *Reprod. Fertil. Dev.* 10:31-47 (1998).
Reynolds, S. et al., "Differentiation-inducing effect of retinoic acid, difluoromethylornithine, sodium butyrate and sodium suramin in human colon cancer cells," *Cancer Lett.* 134(1):53-60 (1998).
Rivero, J. & Adunyah, S., "Sodium butyrate stimulates PKC activation and induces differential expression of certain PKC isoforms during erythroid differentiation," *Biochem. Biophys. Res. Comm.* 248(3):664-68 (1998).
Rocchi, P. et al., "Effect of butyrate analogues on proliferation and differentiation in human neuroblastoma cell lines," 199:1099-103 (1998).
Rogler, L. "Selective bipotential differentiation of mouse embryonic hepatoblasts in vitro," *Am. J. Pathol.* 150(2):591-602 (1997).
Ruhnke, M. et al., "Long-term culture and differentiation of rat embryonic stem cell-like cells into neuronal, glial, endothelial, and hepatic lineages," *Stem Cells* 21:428-36 (2003).
Runge, D. et al., "STAT 1α/1β, STAT 3 and STAT 5: Expression and Association with c-MET and EGF-Receptor in Long-Term Cultures of Human Hepatocytes," *Biochem. Biophys. Res. Comm.* 265:376-81 (1999).
Saito, H. et al., "Changes of antigen expression on human hepatoma cell lines caused by sodium butyrate, a differentiation inducer," *J. Gastroenterol.* 29:733 (1994).
Saito, H. et al., "Differentiating effect of sodium butyrate on human hepatoma cell lines PLC/PRF/5, HCC-M and HCC-T," *Int. J. Cancer* 48(2):291-96 (1991).
Saito, H. et al., "Effect of dexamethasone, dimethylsulfoxide and sodium butyrate on a human hepatoma cell line PLC/PRF/5," *Cancer Biochem. Biophys.* 13:75-84 (1992).
Sánchez, A. et al., "Transforming growth factor-β (TGF-β) and EGF promote cord-like structures that indicate terminal differentiation of fetal hepatocytes in primary culture," *Exp. Cell Res.* 242:27-37 (1998).
Schuldiner, M. et al., "Effects of eight growth factors on the differentiation of cells derived from human embryonic stem cells," *PNAS* 97(21):11307-12 (2000).
Schultz, R. et al., "Reprogramming of gene expression during preimplantation development," *J. Exp. Zool. (Mol. Dev. Evol.)* 285:276-82 (1999).
Shirahashi, H. et al., "Differentiation of human and mouse embryonic stem cells along a hepatocyte lineage," *Cell Transplantation* 13:197-211 (2004).

Siavoshian, S. et al., "Butyrate and trichostatin A effects on the proliferation/differentiation of human intestinal epithelial cells: induction of cyclin D3 and p21 expression," *Gut* 46(4):507-14 (2000).
Simon, B. et al., "Transient transcriptional activation of gastrin during sodium butyrate-induced differentiation of islet cells," *Regul. Pept.* 70:143-48 (1997).
Staecker, J. et al., "Sodium butyrate preserves aspects of the differentiated phenotype of normal adult rat hepatocytes in culture," *J. Cell. Physiol.* 135(3):367-76 (1988).
Staecker, J. et al., "Stimulation of DNA synthesis in primary cultures of adult rat hepatocytes by sodium butyrate," *Biochem. Biophys. Res. Comm.* 147(1):78-85 (1987).
Staecker, J. & Pitot, H., "The effect of sodium butyrate on tyrosine aminotransferase induction in primary cultures of normal adult rat hepatocytes," *Arch. Biochem. Biophys.* 261(2):291-98 (1988).
Strain, A., "Ex vivo liver cell morphogenesis: one step nearer to the bioartificial liver," *Hepatology* 29(1):288-90 (1999).
Sun, S. et al., "Altered phospholipid metabolism in sodium butyrate-induced differentiation of C6 glioma cells," *Lipids* 32(3):273-82 (1997).
Tamagawa, K. et al., "Proanthocyanidins from barley bran potentiate retinoic acid-induced granulocytic and sodium butyrate-induced monocytic differentiation of HL60 cells," *Biosci. Biotechnol. Biochem.* 62(8):1483-87 (1998).
Tanaka, T. et al., "Adenovirus-mediated prodrug gene therapy for carcinoembryonic antigen-producing human gastric carcinoma cells in vitro," *Cancer Res.* 56(6):1341-45 (1996).
Tateno, C. et al., "Growth and differentiation of adult rat hepatocytes regulated by the interaction between parenchymal and non-parenchymal liver cells," *J. Gast. Hepatol.* 13(Suppl.):S83-S92 (1998).
Tateno, C. et al., "Growth potential and differentiation capacity of adult rat hepatocytes in vitro," *Wound Rep. Reg* 7(1):36-44 (1999).
Thomson, et al., "Embryonic stem cell lines derived from human blastocysts," *Science* 282:1145-7 (1998).
Thomson, J. et al., "Neural differentiation of rhesus embryonic stem cells," *APMIS* 106:149-56 (1998).
Trounson, A. & Pera, M., "Potential benfits of cell cloning for human medicine," *Reprod. Fertil. Dev.* 10:121-25 (1998).
Verfaillie, C. et al., "Stem Cells: Hype and Reality," *Hematol. (Am. Soc. Hematol. Educ. Prog.)*, pp. 369-391 (2002).
Wang, G. et al., "Transforming growth factor-β1 acts cooperatively with sodium *n*-butyrate to induce differentiation of normal human keratinocytes," *Exp. Cell Res.* 198(1):27-30 (1992).
Watkins, S. et al., "Butyric acid and tributyrin induce apoptosis in human hepatic tumour cells," *J. Dairy Res.* 66(4):559-67 (1999).
Webster's Online Dictionary, definition for "HeLa cells," one page., 2004.
Yabushita, H. & Sartorelli, A., "Effects of sodium butyrate, dimethylsulfoxide and dibutyryl cAMP on the poorly differentiated ovarian adenocarcinoma cell line AMOC-2," *Oncol. Res.* 5(4-5):173-82 (1993).
Yamada, K. et al., "Effects of butyrate on cell cycle progression and polyploidization of various types of mammalian cells," *Biosci. Biotechnol. Biochem.* 56(8):1261-65 (1992).
Yoon, J-H. et al., "Augmentation of Urea-synthetic Capacity by Inhibition of Nitric Oxide Synthesis in Butyrate-Induced Differentiated Human Hepatocytes," *FEBS Lett.* 474:175-78 (2000).
Yoon, J-H. et al., "Development of a non-transformed human liver cell line with differentiated-hepatocyte and urea-synthetic functions: applicable for bioartificial liver," *Int. J. Artifical Organs* 22(11):769-77 (1999).
Yoshizawa, T. et al., "Dimethylsulfoxide maintains intercellular communication by preserving the gap junctional protein connexin32 in primary cultured hepatocyte doublets from rats," *J. Gastroenterol. Hepatol.* 12:325-30 (1997).
Zaret, K., "Hepatocyte differentiation: from the endoderm and beyond," *Curr. Op. Genet. Dev.* 11:568-74 (2001).
Zvibel, I. et al., "Phenotypic characterization of rat hepatoma cell lines and lineage-specific regulation of gene expression by differentiation agents," *Differentiation* 63:215-23 (1998).

US 8,148,151 B2

DIFFERENTIATION OF PRIMATE PLURIPOTENT CELLS TO HEPATOCYTE-LINEAGE CELLS

This application is a national stage application of PCT International Application No. PCT/US2007/012982 filed Jun. 1, 2007, which claims the benefit of U.S. Provisional Application No. 60/810,416, filed Jun. 2, 2006, both of which are incorporated by reference herein in their entirety for any purpose.

FIELD

This invention relates to the field of in-vitro differentiation of primate pluripotent stem cells into hepatocyte-lineage cells.

BACKGROUND

Cost-effective development of new pharmaceutical agents depends closely on the ability to prescreen drug candidates in high throughput cellular based assays. The compounds are tested not only for their ability to induce the desired effect on the target tissue, but also for a low side-effect profile in unrelated metabolic systems.

Since the liver controls the clearance and metabolism of most small-molecule drugs, a cornerstone of the screening process is to evaluate the effect on liver cells. One objective is to determine whether the compounds or their metabolites have any potential for hepatotoxicity—measured by an effect of the compound on cell viability, morphology, phenotype, or release of metabolites and enzymes that correlate with a compromise in cell function. Another objective is to evaluate the profile of metabolites produced from the compound, since the metabolites may have collateral effects on other cell types.

For this reason, there is a high commercial demand for high quality hepatocytes by the pharmaceutical industry. Tumor cell lines and cells from non-human mammals are often unsuitable for this process, and so pharmaceutical companies are often forced to use clinical samples and primary cultures of human cells. Because of supply and consistency issues, there is a strong need to identify a source that could provide large quantities of human hepatocytes having standardized and reproducible criteria of quality.

Hepatocytes may also be used to make bioartificial organs for clinical use. Such organs are needed to support individuals with impaired liver function as a part of long-term therapy and/or to bridge the time between a fulminant hepatic failure and hepatic reconstitution or liver transplant.

Unfortunately, culture systems for expanding human hepatocytes have been difficult to develop. European Patent Application EP 953 633 A1 proposes a cell culturing method and medium for producing differentiated human liver cells, apparently from donated human liver tissue. In most people's hands, the replication capacity of human hepatocytes in culture has been disappointing. As a remedy, it has been proposed that hepatocytes be immortalized by transfecting with large T antigen of the SV40 virus (U.S. Pat. No. 5,869,243). Alternatively, it has been proposed that a line of hepatocytes be developed that has had its replicative capacity increased using telomerase reverse transcriptase (WO 02/48319).

SUMMARY

The invention provides methods of obtaining hepatocyte-lineage cells comprising sequentially culturing primate pluripotent stem cells in the following order: (a) culturing in a first culture medium comprising an Activin; and (b) culturing in a second culture medium comprising at least one of an HGF polypeptide, an EGF polypeptide, and an OSM polypeptide.

The invention also provides methods of obtaining hepatocyte-lineage cells comprising sequentially culturing primate pluripotent stem cells in the following order: (a) culturing in a first culture medium comprising an Activin and sodium butyrate; (b) culturing in a second culture medium comprising DMSO; (c) culturing in a third culture medium comprising an HGF polypeptide, an EGF polypeptide, and dexamethasone; and (d) culturing in a fourth culture medium comprising an HGF polypeptide, an EGF polypeptide, and an OSM polypeptide.

In certain embodiments, the concentration of the Activin in the first culture medium is 1 ng/ml to 200 ng/ml. In certain embodiments, the concentration of sodium butyrate in the first culture medium is 0.1 mM to 5 mM. In certain embodiments, the concentration of DMSO in the second culture medium is 0.1% to 5%. In certain embodiments, the concentration of the HGF polypeptide in the third culture medium is 1 ng/ml to 100 ng/ml. In certain embodiments, the concentration of the EGF polypeptide in the third culture medium is 1 ng/ml to 100 ng/ml. In certain embodiments, the concentration of dexamethasone in the third culture medium is 0.1 µM to 10 µM. In certain embodiments, the concentration of the HGF polypeptide in the fourth culture medium is 1 ng/ml to 100 ng/ml. In certain embodiments, the concentration of the EGF polypeptide in the fourth culture medium is 1 ng/ml to 100 ng/ml. In certain embodiments, and the concentration of the OSM polypeptide in the fourth culture medium is 1 ng/ml to 100 ng/ml.

In certain embodiments, the concentration of Activin in the first culture medium is 25 ng/ml to 150 ng/ml. In certain embodiments, the concentration of sodium butyrate in the first culture medium is 0.5 mM to 1.5 mM. In certain embodiments, the concentration of DMSO in the second culture medium is 0.5% to 1.5%. In certain embodiments, the concentration of the HGF polypeptide in the third culture medium is 5 ng/ml to 20 ng/ml. In certain embodiments, the concentration of the EGF polypeptide in the third culture medium is 5 ng/ml to 20 ng/ml. In certain embodiments, the concentration of dexamethasone in the third culture medium is 0.5 µM to 2 µM. In certain embodiments, the concentration of the HGF polypeptide in the fourth culture medium is 5 ng/ml to 20 ng/ml. In certain embodiments, the concentration of the EGF polypeptide in the fourth culture medium is 5 ng/ml to 20 ng/ml. In certain embodiments, and the concentration of the OSM polypeptide in the fourth culture medium is 15 ng/ml to 35 ng/ml.

The invention also provides methods of obtaining hepatocyte-lineage cells comprising sequentially culturing primate pluripotent stem cells in the following order: (a) culturing in a first culture medium comprising an Activin; (b) culturing in a second culture medium comprising DMSO; and (c) culturing in a third culture medium comprising an HGF polypeptide and an OSM polypeptide.

In certain embodiments, the concentration of the Activin in the first culture medium is 1 ng/ml to 200 ng/ml. In certain embodiments, the concentration of DMSO in the second culture medium is 0.1% to 5%. In certain embodiments, the concentration of the HGF polypeptide in the third culture medium is 1 ng/ml to 100 ng/ml. In certain embodiments, the concentration of the OSM polypeptide in the third culture medium is 1 ng/ml to 100 ng/ml.

In certain embodiments, the concentration of Activin in the first culture medium is 25 ng/ml to 150 ng/ml. In certain embodiments, the concentration of DMSO in the second culture medium is 0.5% to 1.5%. In certain embodiments, the concentration of the HGF polypeptide in the third culture medium is 5 ng/ml to 20 ng/ml. In certain embodiments, and the concentration of the OSM polypeptide in the third culture medium is 15 ng/ml to 35 ng/ml.

The invention also provides methods of obtaining hepatocyte-lineage cells comprising sequentially culturing primate pluripotent stem cells in the following order: (a) culturing in a first culture medium comprising an Activin and sodium butyrate; (b) culturing in a second culture medium comprising DMSO; and (c) culturing in a third culture medium comprising an HGF polypeptide and an OSM polypeptide.

In certain embodiments, the concentration of the Activin in the first culture medium is 1 ng/ml to 200 ng/ml. In certain embodiments, the concentration of sodium butyrate in the first culture medium is 0.1 mM to 5 mM. In certain embodiments, the concentration of DMSO in the second culture medium is 0.1% to 5%. In certain embodiments, the concentration of the HGF polypeptide in the third culture medium is 1 ng/ml to 100 ng/ml. In certain embodiments, the concentration of the OSM polypeptide in the third culture medium is 1 ng/ml to 100 ng/ml.

In certain embodiments, the concentration of Activin in the first culture medium is 25 ng/ml to 150 ng/ml. In certain embodiments, the concentration of sodium butyrate in the first culture medium is 0.5 mM to 1.5 mM. In certain embodiments, the concentration of DMSO in the second culture medium is 0.5% to 1.5%. In certain embodiments, the concentration of the HGF polypeptide in the third culture medium is 5 ng/ml to 20 ng/ml. In certain embodiments, and the concentration of the OSM polypeptide in the third culture medium is 15 ng/ml to 35 ng/ml.

In certain embodiments, the Activin comprises at least one of Activin A, Activin B, and Activin C. In certain embodiments, the Activin comprises an Activin peptide. In certain embodiments, the Activin comprises an active fragment of at least one of Activin A, Activin B, and Activin C. In certain embodiments, the Activin comprises an active protein that is at least 95% identical to at least one of Activin A, Activin B, and Activin C. In certain embodiments, the Activin is Activin A.

In certain embodiments, the HGF polypeptide is an HGF. In certain embodiments, the HGF polypeptide is an active fragment of an HGF. In certain embodiments, the HGF polypeptide is an active protein that is 95% identical to an HGF.

In certain embodiments, the EGF polypeptide is an EGF. In certain embodiments, the EGF polypeptide is an active fragment of an EGF. In certain embodiments, the EGF polypeptide is an active protein that is 95% identical to an EGF.

In certain embodiments, the OSM polypeptide is an OSM. In certain embodiments, the OSM polypeptide is an active fragment of an OSM. In certain embodiments, the OSM polypeptide is an active protein that is 95% identical to an OSM.

In addition, the invention provides methods of obtaining hepatocyte-lineage cells comprising sequentially culturing primate pluripotent stem cells in the following order: (a) culturing in a first culture medium comprising 100 ng/ml Activin A and 1 mM sodium butyrate; (b) culturing in a second culture medium comprising 100 ng/ml Activin A and 0.5 mM sodium butyrate; (c) culturing in a third culture medium comprising 1% DMSO; (d) culturing in a fourth culture medium comprising 10 ng/ml HGF, 10 ng/ml EGF, and 1 µm dexamethasone; and (e) culturing in a fifth culture medium comprising 10 ng/ml HGF, 10 ng/ml EGF, and 25 ng/ml OSM.

The invention also provides methods of obtaining hepatocyte-lineage cells comprising sequentially culturing primate pluripotent stem cells in the following order: (a) culturing in a first culture medium comprising 100 ng/ml Activin A and 1 mM sodium butyrate; (b) culturing in a second culture medium comprising 100 ng/ml Activin A and 0.5 mM sodium butyrate; (c) culturing in a third culture medium comprising 1% DMSO; (d) culturing in a fourth culture medium comprising 10 ng/ml HGF and 20 ng/ml OSM.

DESCRIPTION OF THE FIGURES

FIG. 4B shows a summary of the relative level of expression of HNF4α, AFP, and albumin (ALB) at each stage.

DETAILED DESCRIPTION OF CERTAIN EMBODIMENTS

Definitions

Figure 1:
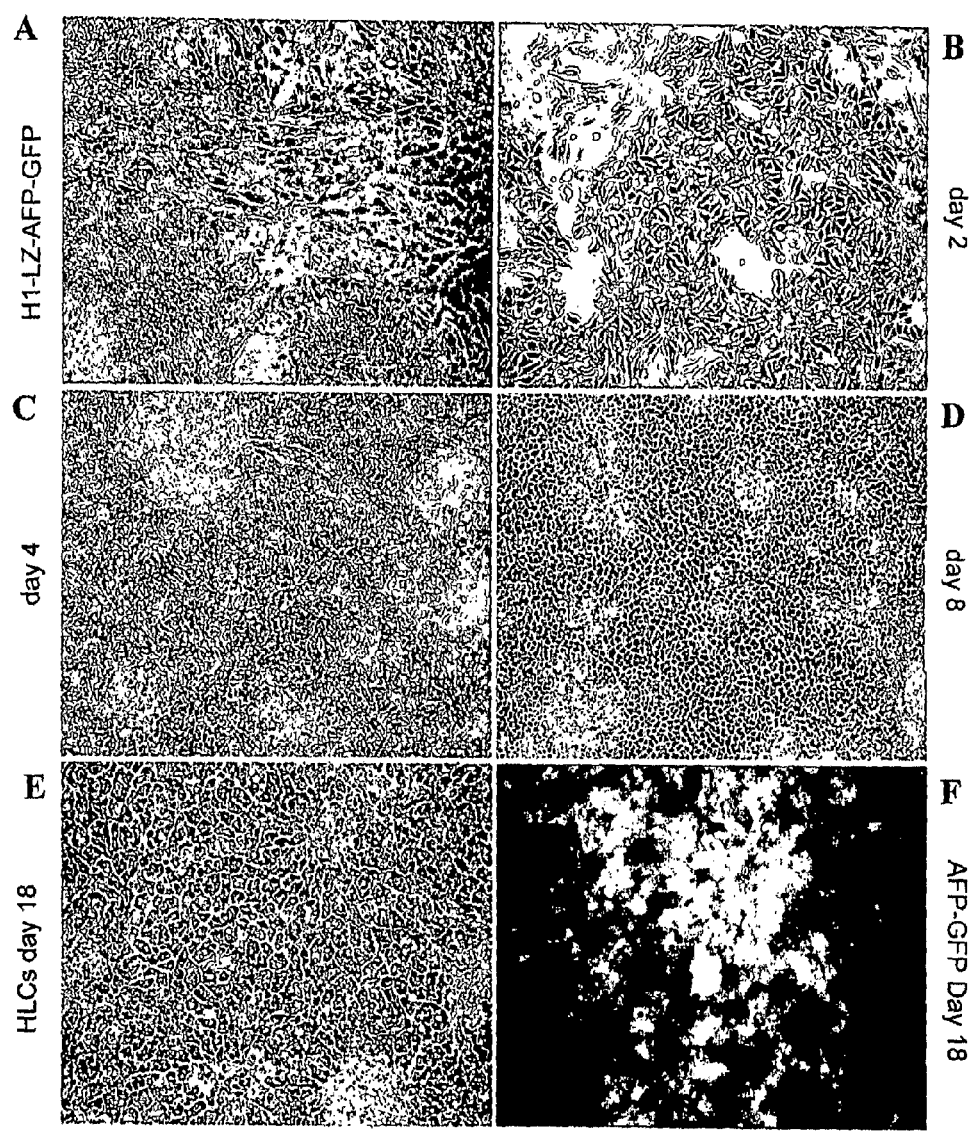
FIG. 1 shows differentiation of H1 hES cells to hepatocyte-lineage cells as discussed in Example 1. Panel A shows the H1 hES cells prior to the differentiation protocol. Panel B shows the cells at day 2 of the protocol. Panel C shows the cells at day 4 of the protocol. Panel D shows the cells at day 8 of the protocol. Panel E shows the cells at day 18 of the protocol. Panel F shows GFP expression in the cells, wherein GFP expression is driven by an AFP promoter, at day 18 of the protocol.

The term "hepatocyte-lineage cells", as defined herein, refers to cells derived from primate pluripotent stem cells, and which express albumin and at least one P450 isozyme selected from CYP2C9, CYP2C19, CYP3A7, and CYP3A4. In certain embodiments, hepatocyte-lineage cells also express one or more markers selected from PXR, α-antitrypsin, glucose-6-phosphatase, catalase, H.2, H.4, H-6, HES6, and RL23/36. Hepatocyte-lineage cells include hepatocyte precursor cells, immature hepatocytes, and mature hepatocytes.

In certain embodiments, hepatocyte-lineage cells exhibit one or more of the following morphological features: a polygonal cell shape, a binucleate phenotype, the presence of rough endoplasmic reticulum, the presence of Golgi-endoplasmic reticulum lysosome complex, the presence of peroxisomes and glycogen granules, and the ability to form tight intercellular junctions resulting in creation of bile canalicular spaces. In certain embodiments, hepatocyte-lineage cells exhibit at least two, at least three, at least four, or at least five of those features.

The term "embryoid bodies" refers to heterogeneous clusters comprising differentiated and partly differentiated cells that appear when primate pluripotent stem cells are allowed to differentiate in a non-specific fashion in suspension cultures or monolayer cultures.

As used herein, "primate pluripotent stem cells" or "pPs cells" refer to primate cells that are capable upon differentiation of producing cell types that are derivatives of all of the 3 germinal layers (endoderm, mesoderm, and ectoderm). One exemplary test is the ability to form teratomas in 8-12 week old SCID mice. See, e.g., Przyborski, S. A., *Stem Cells* 23:1242-50 (2005).

Exemplary primate pluripotent stem cells include, but are not limited to, human pluripotent stem cells and monkey pluripotent stem cells (including, but not limited to macaque pluripotent stem cells). Included in the definition of primate pluripotent stem cells are embryonic cells of various types, exemplified by, but not limited to, human embryonic stem (hES) cells, (see, e.g., Thomson et al. (Science 282:1145, 1998)) and human embryonic germ (hEG) cells (see, e.g., Shamblott et al., Proc. Natl. Acad. Sci. USA 95:13726, 1998); embryonic stem cells from other primates, such as Rhesus stem cells (see, e.g., Thomson et al., Proc. Natl. Acad. Sci. USA 92:7844, 1995), and marmoset stem cells (see, e.g., Thomson et al., Biol. Reprod. 55:254, 1996).

As used herein, "human embryonic stem cell" or "hES cell" refers to pluripotent stem cells that are derived from a human embryo at the blastocyst stage, or the pluripotent progeny thereof. Except where explicitly stated otherwise, the term includes primary tissue and established lines that bear phenotypic characteristics of hES cells, and progeny of such lines that still have the capacity of producing cells of each of the three germ layers. Certain "human Embryonic Stem cells" (hES cells) are described by Thomson et al. (Science 282:1145, 1998; U.S. Pat. No. 6,200,806; Curr. Top. Dev. Biol. 38:133 ff., 1998) and Reubinoff et al. (Nature Biotech: 18:399, 2000).

As used herein, "direct differentiation" refers to a process for differentiating primate pluripotent stem cells into progeny that are enriched for cells of a particular lineage without forming embryoid bodies as an intermediate. The term direct differentiation encompasses processes in which a small number of cell aggregates form inadvertently.

As used herein, "genetically altered," "transfected," or "genetically transformed" refer to a process where a polynucleotide has been transferred into a cell by any suitable means of artificial manipulation, or where the cell is a progeny of the originally altered cell and has inherited all or part of the polynucleotide. The polynucleotide may comprise a transcribable sequence encoding a protein of interest, which enables the cell to express the protein. In certain embodiments, the polynucleotide comprises a sequence encoding a molecule such as siRNA or antisense RNA that affects the expression of a protein (either an endogenous protein or an exogenous protein, e.g., that is expressed as the result of the introduction of a polynucleotide sequence). The genetic alteration is said to be "inheritable" if progeny of the altered cell have the same alteration.

As used herein, "serum-free" refers to a condition where the referenced composition contains no added serum.

As used herein, "feeder-free" refers to a condition where the referenced composition contains no added feeder cells. The term feeder-free encompasses, inter alia, situations where primate pluripotent stem cells are passaged from a culture with feeders into a culture without added feeders even if some of the feeders from the first culture are present in the second culture. The term feeder-free also encompasses situations where some of the cultured primate pluripotent stem cells have themselves differentiated into feeder cells.

Expression of an antigen by a cell is said to be "antibody-detectable" if the antibody will bind to the antigen in a standard immunocytochemistry or flow cytometry assay, optionally after fixing the cells, at a level that is at least 2-fold above the background level of binding by a control antibody. In various embodiments, the level of antibody binding is at least 5 fold or at least 10 fold above the background level of binding by the control antibody. Control antibodies include, but are not limited to, antibodies to antigens that are predicted not to be present in the selected cell population.

DETAILED DESCRIPTION OF CERTAIN EMBODIMENTS

Methods for producing hepatocyte-lineage cells from primate pluripotent stem cells (pPS cells) are provided herein. Such methods may comprise culturing the pPS cells in the presence of Activin, followed by culturing in one or more growth factors.

General Techniques

For further elaboration of general techniques useful in the practice of this invention, one skilled in the art can refer to standard textbooks and reviews, for example, in the fields of cell biology, tissue culture, embryology, and cardiophysiology.

With respect to tissue and cell culture and embryonic stem cells, one skilled in the art may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998; and R. I. Freshney, Culture of Animal Cells, Wiley-Liss, New York, 2000). General methods in molecular and cellular biochemistry can be found in standard textbooks, including but not limited to, *Short Protocols in Molecular Biology*, 4*th* Ed.; *Immunology Methods Manual* (I. Lefkovits ed., Academic Press 1997); and *Cell and Tissue Culture: Laboratory Procedures in Biotechnology* (Doyle & Griffiths, John Wiley & Sons 1998).

Certain additional reference books include, but are not limited to, *The Hepatocyte Review*, M. N. Berry & A. M. Edwards Eds., Kluwer Academic Publishers, 2000; *Hepatocyte Transplantation* (*Falk Symposium*, 126), S. Gupta, J. Klempnauer, P. L. M. Jansen, M. P. Manns Eds., Kluwer Academic Publishers, 2002; *Handbook of Drug Screening*, R. Seethala & P. B. Fernandes Eds., Marcel Dekker, 2001; and *Bioassay Techniques for Drug Development*, Atta-Ur-Rahman, M. I. Choudhary, W. J. Thomsen, A. Rahman, Taylor & Francis, 2001.

Certain Exemplary Reagents

As used herein, "Activin" refers to a primate polypeptide growth factor comprising at least one of Activin A, Activin B, Activin C, an active fragment of any of those Activins, and/or an active protein that is at least 95% identical to Activin A, Activin B, and/or Activin C. As used herein, "Activin peptide" refers to a primate polypeptide growth factor comprising at least one of Activin A, Activin B, Activin C, and/or an active fragment of any of those Activins. In certain embodiments, Activin is a dimer selected from an Activin A homodimer, an Activin B homodimer, an Activin AB heterodimer, an Activin C homodimer. In certain embodiments, Activin is selected from one of the aforementioned dimers in which one or both polypeptides is an active fragment of Activin A, B, or C. In certain embodiments, an Activin and/or Activin peptide is a human Activin and/or Activin fragment having Activin activity.

A fragment of Activin A, Activin B, or Activin C, or a protein that is at least 95% identical to Activin A, Activin B, and/or Activin C is considered to be active if cells that express albumin and at least one P450 isozyme selected from CYP2C9, CYP2C19, CYP3A7, and CYP3A4 are produced when the protocol described in Example 1 is carried out, but with the Activin A in the protocol replaced with the fragment of Activin A, Activin B, or Activin C, and/or the protein that is at least 95% identical to Activin A, Activin B, and/or Activin C being tested.

As used herein, "HGF" refers to a hepatocyte growth factor. In certain embodiments, an HGF is a human or primate HGF. As used herein, "HGF polypeptide" refers to an HGF, an active fragment of an HGF, and/or an active protein that is at least 95% identical to an HGF. A human HGF polypeptide refers to a human HGF, an active fragment of human HGF, and/or an active protein that is at least 95% identical to a human HGF.

A fragment of an HGF, or a protein that is at least 95% identical to an HGF is considered to be active if cells that express albumin and at least one P450 isozyme selected from CYP2C9, CYP2C19, CYP3A7, and CYP3A4 are produced when the protocol described in Example 1 is carried out, but with the HGF in the protocol replaced with the fragment of an HGF, or the protein that is at least 95% identical to an HGF being tested.

As used herein, "EGF" refers to an epidermal growth factor. In certain embodiments, an EGF is a human or primate EGF. As used herein, "EGF polypeptide" refers to an EGF, an active fragment of an EGF, and/or an active protein that is at least 95% identical to an EGF. A human EGF polypeptide refers to a human EGF, an active fragment of human EGF, and/or an active protein that is at least 95% identical to a human EGF.

A fragment of an EGF, or a protein that is at least 95% identical to an EGF is considered to be active if cells that express albumin and at least one P450 isozyme selected from CYP2C9, CYP2C19, CYP3A7, and CYP3A4 are produced when the protocol described in Example 1 is carried out, but with the EGF in the protocol replaced with the fragment of an EGF, or the protein that is at least 95% identical to an EGF being tested.

As used herein, "bFGF" or "FGF2" refers to a basic fibroblast growth factor. In certain embodiments, a bFGF is a human or primate bFGF. As used herein, "bFGF polypeptide" or "FGF2 polypeptide" refers to a bFGF, an active fragment of a bFGF, and/or an active protein that is at least 95% identical to a bFGF. A human bFGF polypeptide refers to a human bFGF, an active fragment of human bFGF, and/or an active protein that is at least 95% identical to a human bFGF.

A fragment of a bFGF, or a protein that is at least 95% identical to a bFGF is considered to be active if cells that express albumin and at least one P450 isozyme selected from CYP2C9, CYP2C19, CYP3A7, and CYP3A4 are produced when the protocol described in Example 1 is carried out, but with the bFGF in the protocol replaced with the fragment of a bFGF, or the protein that is at least 95% identical to a bFGF being tested.

As used herein, "OSM" refers to an Oncostatin M. In certain embodiments, an OSM is a human or primate OSM. As used herein, "OSM polypeptide" refers to an OSM, an active fragment of an OSM, and/or an active protein that is at least 95% identical to an OSM. A human OSM polypeptide refers to a human OSM, an active fragment of human OSM, and/or an active protein that is at least 95% identical to a human OSM.

A fragment of an OSM, or a protein that is at least 95% identical to an OSM is considered to be active if cells that express albumin and at least one P450 isozyme selected from CYP2C9, CYP2C19, CYP3A7, and CYP3A4 are produced when the protocol described in Example 1 is carried out, but with the OSM in the protocol replaced with the fragment of an OSM, or the protein that is at least 95% identical to an OSM being tested.

As used herein, "dexamethasone" refers to 9-fluoro-11β, 17,21-trihydroxy-16a-methylpregna-1,4-diene-3,20-dione (CAS No. 50-02-2) and analogs and derivatives thereof that retain at least 50% of the activity of 9-fluoro-11β,17,21-trihydroxy-16a-methylpregna-1,4-diene-3,20-dione.

As used herein, "sodium butyrate" refers to a chemical having the formula $CH_3CH_2CH_2COONa$.

As used herein, "dimethyl sulfoxide" or "DMSO" refers to a chemical having the formula $(CH_3)_2SO$.

As used herein, the "culture medium" refers to liquid media used to culture and differentiate primate pluripotent stem cells. Exemplary culture media are based on basic media including, but are not limited to, RPMI-1640 (Sigma cat. no. RS886), Knockout™ DMEM (GibcoBRL/Invitrogen cat no. 10829-018), and HCM Bullet Kit (Cambrex/Clonetics/Biowhittaker cat no. CC-3198). In certain embodiments, one or more supplements are added to the basic media to form the culture media. Exemplary supplements that may be included in the culture media for one or more periods of time during the methods described herein include, but are not limited to, B27 Supplement without vitamin A (e.g., GibcoBRL/Invitrogen cat. no. 12587-010), N2 supplement (GibcoBRL/Invitrogen cat. no. 17502-048), and G5 supplement (GibcoBRL/Invitrogen cat. no. 17503-012), L-glutamine (e.g., 200 mM solution, GibcoBRL/Invitrogen cat. no. 25030-81), non-essential amino acids (e.g., GibcoBRL/Invitrogen cat. no. 11140-050), and β-mercaptoethanol (e.g., Sigma cat. no. M7522).

As used herein "serum replacement" refers to a composition added to the culture media that mimics serum, but is not derived from animal products. Exemplary serum replacements include, but are not limited to, Knockout™ Serum Replacement (GibcoBRL/Invitrogen cat. no. 10828-028).

As used herein, "basement membrane matrix" or "extracellular matrix" refers to a composition used in vitro to mimic the in vivo mammalian cellular basement membrane. Exemplary basement membrane matrices include, but are not limited to, BD Matrigel™ Basement Membrane Matrix (Becton, Dickinson Co., Franklin Lakes, N.J.) ("Matrigel"). In certain embodiments, a basement membrane matrix comprises one or more of laminin, collagen IV, heparan sulfate proteoglycans, and entactin. In certain embodiment, a basement membrane matrix is derived from Engelbreth-Holm-Swarm tumor cells.

As used herein, "feeder cells" refers to cells of a first tissue type that may act to promote proliferation and/or control differentiation of cells of a second tissue type when the cells are cocultured together. In certain embodiments, the feeder cells are of a different cell type than the cocultured cells. For example, primate pluripotent stem cells can be cocultured with embryonic fibroblasts of the same, or different species. In various embodiments, feeder cells may help maintain the undifferentiated state of primate pluripotent stem cells or may help direct differentiation towards a particular tissue type (e.g., hepatocyte-lineage cells). In certain embodiments, feeder cells may be differentiated from primate pluripotent stem cells. See, e.g., WO01/51616.

Primate Pluripotent Stem Cells

Methods for differentiating primate pluripotent stem cells into hepatocyte-lineage cells are provided. Primate pluripotent stem cells that may be used in the methods include, but are not limited to, embryonic stem cells. Embryonic stem cells can be isolated, e.g., from blastocysts of primate species (see, e.g., U.S. Pat. No. 5,843,780; Thomson et al., Proc. Natl. Acad. Sci. USA 92:7844, 1995). Human embryonic stem (hES) cells can be prepared, e.g., from human blastocyst cells using, for example, the techniques described by Thomson et al. (U.S. Pat. No. 6,200,806; Science 282:1145, 1998; Curr. Top. Dev. Biol. 38:133 ff., 1998) and Reubinoff et al. (Nature Biotech. 18:399, 2000). Certain other primate pluripotent stem cell types include, but are not limited to, primitive ectoderm-like (EPL) cells (see, e.g., WO 01/51610 (Bresagen)) and human embryonic germ (hEG) cells (see, e.g., Shamblott et al., Proc. Natl. Acad. Sci. USA 95:13726, 1998).

Embryonic stem cells may be chosen from embryonic stem cell lines or may be obtained directly from primary embryonic tissue. A number of embryonic stem cell lines have been established including, but not limited to, H1, H7, H9, H13 and H14 (Thompson et al.); hESBGN-01, hESBGN-02, hESBGN-03 (BresaGen, Inc., Athens, Ga.); HES-1, HES-2, HES-3, HES-4, HES-5, HES-6 (ES Cell International, Inc., Singapore); HSF-1, HSF-6 (University of California at San Francisco); I 3, I 4, I 6 (Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005).

In certain embodiments, primate pluripotent stem cells may have been derived in a feeder-free manner (see, e.g., Klimanskaya et al., Lancet, 365(9471):1636-41 (2005)).

Primate Pluripotent Stem Cell Culture

Primate pluripotent stem cells may be cultured using a variety of substrates, media, and other supplements and factors known in the art. Primate pluripotent stem cells can be propagated continuously in culture, using culture conditions that promote proliferation while inhibiting differentiation. Exemplary media include 80% DMEM (such as Knock-Out DMEM, GibcoBRL), 20% of either defined fetal bovine serum (FBS, Hyclone) or serum replacement (US 2002/0076747 A1, Life Technologies Inc.), 1% non-essential amino acids, 1 mM L-glutamine, 0.1 mM β-mercaptoethanol, and 4 ng/ml bFGF (GibcoBRL/Invitrogen). The media is conditioned by overnight culture with mitotically inactivated mouse embryonic fibroblasts. An additional 8 ng/ml bFGF was add to the media before it was used for pluripotent stem cell culture.

In certain embodiments, primate pluripotent stem cells are cultured on a layer of feeder cells, typically fibroblasts derived from embryonic or fetal tissue (see, e.g., Thomson et al., Science 282:1145, 1998). In certain embodiments, those feeder cells are of human or mouse origin. Human feeder cells can be isolated from various human tissues or derived by differentiation of human embryonic stem cells into fibroblast cells (see, e.g., WO01/51616). In certain embodiments, human feeder cells include, but are not limited to, placental fibroblasts (see, e.g., Genbacev et al., Fertil. Steril. 83(5): 1517-29, 2005), fallopian tube epithelial cells (see, e.g., Richards et al., Nat. Biotechnol., 20:933-36, 2002), foreskin fibroblasts (see, e.g., Amit et al., Biol. Reprod. 68:2150-56, 2003), and uterine endometrial cells (see, e.g., Lee et al., Biol. Reprod. 72(1):42-49, 2005)

In certain embodiments, primate pluripotent stem cells may be maintained in an undifferentiated state without added feeder cells (see, e.g., Rosier et al., Dev. Dynam. 229:259-274, 2004). Feeder-free cultures are typically supported by a nutrient medium containing factors that promote proliferation of the cells without differentiation (see, e.g., U.S. Pat. No. 6,800,480). In certain embodiments, such factors may be introduced into the medium by culturing the medium with cells secreting such factors, such as irradiated (~4,000 rad) primary mouse embryonic fibroblasts, telomerized mouse fibroblasts, or fibroblast-like cells derived from primate pluripotent stem cells (see, e.g., U.S. Pat. No. 6,642,048). Medium can be conditioned, e.g., by plating the feeders in a serum free medium such as KO DMEM supplemented with 20% serum replacement and 4 ng/mL bFGF. Medium that has been conditioned for 1-2 days is supplemented with further bFGF, and used to support primate pluripotent stem cell culture for 1-2 days (see, e.g., WO 01/51616; Xu et al., Nat. Biotechnol. 19:971, 2001).

Alternatively, fresh or non-conditioned medium can be used, which has been supplemented with added factors (such as, for example, fibroblast growth factor and/or forskolin) that promote proliferation of the cells in an undifferentiated form. An exemplary non-conditioned medium includes a base medium like X-VIVO™ 10 (Biowhittaker) or QBSF™-60 (Quality Biological Inc.), supplemented with bFGF at 40-100 ng/mL, and optionally containing stem cell factor (15 ng/mL), noggin (0.5 μg/mL), or Flt3 ligand (75 ng/mL) (see, e.g., Xu et al., Stem Cells 23(3):315-23, 2005; Xu et al., Nature Methods 2(3): 185-90 (2005)). These medium formulations have the advantage of supporting cell growth at 2-3 times the rate of other systems (see, e.g., WO 03/020920).

Certain nonlimiting exemplary pluripotent stem cell culture methods follow. The primate pluripotent stem cells are plated at >15,000 cells cm$^{-2}$ (for example, 90,000 cm$^{-2}$ to 170,000 cm$^{-2}$). Enzymatic digestion, with trypsin, may be halted before cells become completely dispersed (e.g., ~5 min with collagenase IV). Clumps of ~0.10 to 2,000 cells may be plated directly onto the substrate without further dispersal. Alternatively, the cells may be harvested without enzymes before the plate reaches confluence by incubating ~5 min in a solution of 0.5 mM EDTA in PBS or by simply detaching the desired cells from the plate mechanically, such as by scraping or isolation with a fine pipet. After washing from the culture vessel, the cells may be plated into a new culture without further dispersal. In a further illustration, confluent human embryonic stem cells cultured in the absence of feeders may be removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells cm$^{-2}$.

Under the microscope, primate pluripotent stem cells appear with high nuclear/cytoplasmic ratios, prominent nucleoli, and compact colony formation with poorly discernable cell junctions. Primate pluripotent stem cells may express certain stage-specific embryonic antigens, including, but not limited to, SSEA 3, and SSEA 4, and certain markers detectable using antibodies designated Tra-1-60 and Tra-1-81. In certain embodiments, human embryonic stem cells express the transcription factor Oct-3/4, Cripto, gastrin-releasing peptide (GRP) receptor, podocalyxin-like protein (PODXL), and human telomerase reverse transcriptase (hTERT) (see, e.g., US 2003/0224411 A1), as detected by RT-PCR.

Differentiation of Primate Pluripotent Stem Cells to Hepatocyte-Lineage Cells

Methods for differentiating primate pluripotent stem cells into hepatocyte-lineage cells are provided. In particular, the invention provides methods for differentiating primate pluripotent stem cells into hepatocyte-lineage cells comprising culturing in the presence of an Activin, followed by culturing in at least one growth factor selected from an HGF polypeptide, an EGF polypeptide, and an OSM polypeptide. In certain embodiments, the method comprises the sequential culturing of the primate pluripotent stem cells first in the presence of sodium butyrate and an Activin, then in the presence of DMSO, then in the presence of an HGF polypeptide, an EGF polypeptide, and dexamethasone, and finally in the presence of an HGF polypeptide, an EGF polypeptide, and an OSM polypeptide.

An exemplary culture protocol for differentiating primate pluripotent stem cells to hepatocyte-lineage cells is as follows. hES cells are cultured in the presence of 1 mM sodium butyrate and 100 ng/ml Activin A for 1 day. The cells are then cultured in the presence of 0.5 mM sodium butyrate and 100 ng/ml Activin A for 2 days. The cells are then cultured in the presence of 1% DMSO for 7 days. The cells are then cultured in the presence of 10 ng/ml HGF, 10 ng/ml EGF, and 1 µM dexamethasone for 10 days. Finally, the cells are cultured in the presence of 10 ng/ml HGF, 10 ng/ml EGF, and 25 ng/ml OSM for at least 10 days.

In certain embodiments, at least one Activin is included in the culture medium for between 1 and 10 days, or between 1 and 5 days. In certain embodiments, at least one Activin is included in the culture medium for 1, 2, 3, 4, or 5 days. In certain embodiments, at least one Activin is included in the culture medium for less than one day or more than 5 days. In certain embodiments, a first concentration of one or more Activins is included in the culture medium for a first period of time and a second concentration of one or more Activins is included in the culture medium for a second period of time.

In certain embodiments, at least one Activin is included in the culture medium at a concentration between 1 ng/ml and 200 ng/ml, or between 10 ng/ml and 200 ng/ml, or between 25 ng/ml and 150 ng/ml. In certain embodiments, at least one Activin is included in the culture medium at a concentration below 10 ng/ml or above 200 ng/ml. As a nonlimiting example, 100 ng/ml total concentration of one or more Activins may be included in the culture medium for a total of three days, although other components may be added, removed, or change concentrations at any point or points during that time.

In certain embodiments, at least one Activin used in the differentiation comprises an Activin selected from Activin A, Activin B, Activin AB, and Activin C. In certain embodiments, at least one Activin used in the differentiation comprises an active fragment of Activin A, Activin B, or Activin C. In certain embodiments, at least one Activin used in the differentiation comprises an active protein that is at least 95% identical to Activin A, Activin B, and/or Activin C. In certain embodiments, an Activin used in the differentiation protocol is Activin A, an active fragment of Activin A, or an active protein that is at least 95% identical to Activin A. In certain embodiments, an Activin used in the differentiation protocol is an Activin peptide. In certain embodiments, an Activin used in the differentiation protocol is a human Activin. In certain embodiments, one Activin is used in the differentiation method. In certain embodiments, more than one Activin is used.

In certain embodiments, sodium butyrate is included in the culture medium for between 1 and 10 days, or between 1 and 5 days. In certain embodiments, sodium butyrate is included in the culture medium for 1, 2, 3, 4, or 5 days. In certain embodiments, sodium butyrate is included in the culture medium for less than one day or more than 5 days. In certain embodiments, a first concentration of sodium butyrate is included in the culture medium for a first period of time and a second concentration of sodium butyrate is included in the culture medium for a second period of time.

In certain embodiments, sodium butyrate is included in the culture medium at a concentration between 0.1 mM and 5 mM, or between 0.1 mM and 2 mM, or between 0.5 mM and 1.5 mM. In certain embodiments, sodium butyrate is included in the culture medium at a concentration of 0.2 mM, 0.3 mM, 0.5 mM, 0.75 mM, 1 mM, 1.25 mM, 1.75 mM, or 2 mM. In certain embodiments, sodium butyrate is included in the culture medium at a concentration of below 0.1 mM or above 5 mM. As a nonlimiting example, 1 mM sodium butyrate may be included in the culture medium for one day, and then 0.5 mM sodium butyrate may be included in the culture medium for two days. Other components may be added, removed, or change concentrations at any point or points during that time. In certain embodiments, Activin and sodium butyrate are included in the culture medium at the same time, although each may also be included without the other at one or more times during the same culture protocol.

In certain embodiments, DMSO is included in the culture medium for between 2 and 15 days, or between 5 and 10 days. In certain embodiments, DMSO is included in the culture medium for 7 days. In certain embodiments, a first concentration of DMSO is included in the culture medium for a first period of time and a second concentration of DMSO is included in the culture medium for a second period of time.

In certain embodiments, DMSO is included in the culture medium at a concentration between 0.1% and 5%, between 0.5% and 2.5%, or between 0.5% and 1.5%. In certain embodiments, DMSO is included in the culture medium at a concentration of 1%. As a nonlimiting example, 1% DMSO may be included in the culture medium for a total of 7 days, although other components may be added, removed, or change concentrations at any point or points during that time.

In certain embodiments, an HGF polypeptide is included in the culture medium for between 5 and 100 days, or between 5 and 50 days, or between 10 and 50 days. In certain embodiments, an HGF polypeptide is included in the culture medium for at least 20 days. In certain embodiments, an HGF polypeptide is included in the culture medium for at least 15 days. In certain embodiments, an HGF polypeptide is included in the culture medium for at least 10 days. In certain embodiments, an HGF polypeptide is included in the culture medium for less than 5 days or more than 100 days. In certain embodiments, a first concentration of an HGF polypeptide is included in the culture medium for a first period of time and a second concentration of an HGF polypeptide is included in the culture medium for a second period of time.

In certain embodiments, an HGF polypeptide is included in the culture medium at a concentration between 1 ng/ml and 100 ng/ml, or between 5 ng/ml and 50 ng/ml, or between 5 ng/ml and 20 ng/ml. In certain embodiments, an HGF polypeptide is included in the culture medium below 1 ng/ml or above 100 ng/ml. As a nonlimiting example, 10 ng/ml an HGF polypeptide may be included in the culture medium for a total of 20 days, although other components may be added, removed, or change concentrations at any point or points during that time.

In certain embodiments, the HGF polypeptide used in the differentiation protocol is an HGF. In certain embodiments, the HGF polypeptide used in the differentiation protocol is a human HGF. In certain embodiments, the HGF polypeptide used in the differentiation protocol is a fragment of an HGF. In certain embodiments, the HGF polypeptide used in the differentiation protocol is an active protein that is at least 95% identical to an HGF.

In certain embodiments, an EGF polypeptide is included in the culture medium for between 5 and 100 days, or between 5 and 50 days, or between 10 and 50 days. In certain embodiments, an EGF polypeptide is included in the culture medium for at least 20 days. In certain embodiments, an EGF polypeptide is included in the culture medium for at least 15 days. In certain embodiments, an EGF polypeptide is included in the culture medium for at least 10 days. In certain embodiments, an EGF polypeptide is included in the culture medium for less than 5 days or more than 100 days. In certain embodiments, a first concentration of an EGF polypeptide is included in the culture medium for a first period of time and a second Concentration of an EGF polypeptide is included in the culture medium for a second period of time.

In certain embodiments, an EGF polypeptide is included in the culture medium at a concentration between 1 ng/ml and 100 ng/ml, or between 5 ng/ml and 50 ng/ml, or between 5 ng/ml and 20 ng/ml. In certain embodiments, an EGF polypeptide is included in the culture medium below 1 ng/ml or above 100 ng/ml. As a nonlimiting example, 10 ng/ml an EGF polypeptide may be included in the culture medium for a total of 20 days, although other components may be added, removed, or change concentrations at any point or points during that time.

In certain embodiments, the EGF polypeptide used in the differentiation protocol is an EGF. In certain embodiments, the EGF polypeptide used in the differentiation protocol is a human EGF. In certain embodiments, the EGF polypeptide used in the differentiation protocol is a fragment of an EGF. In certain embodiments, the EGF polypeptide used in the differentiation protocol is an active protein that is at least 95% identical to an EGF.

In certain embodiments, dexamethasone is included in the culture medium for between 5 and 50 days, or between 5 and 20 days, or between 5 and 15 days. In certain embodiments, dexamethasone is included in the culture medium for at least 10 days. In certain embodiments, dexamethasone is included in the culture medium for at least 5 days. In certain embodiments, dexamethasone is included in the culture medium for less than 5 days or more than 50 days. In certain embodiments, a first concentration of dexamethasone is included in the culture medium for a first period of time and a second concentration of dexamethasone is included in the culture medium for a second period of time.

In certain embodiments, dexamethasone is included in the culture medium at a concentration between 0.1 µM and 10 µM, or between 0.1 µM and 5 µM, or between 0.5 µM and 2 µM. In certain embodiments, dexamethasone is included in the culture medium at a concentration less than 0.1 µM or greater than 10 µM. As a nonlimiting example, 1 µM dexamethasone may be included in the culture medium for a total of 10 days, although other components may be added, removed, or change concentrations at any point or points during that time.

In certain embodiments, an OSM polypeptide is included in the culture medium for between 5 and 100 days, or between 5 and 50 days, or between 5 and 20 days. In certain embodiments, an OSM polypeptide is included in the culture medium for at least 20 days. In certain embodiments, an OSM polypeptide is included in the culture medium for at least 15 days. In certain embodiments, an OSM polypeptide is included in the culture medium for at least 10 days. In certain embodiments, an OSM polypeptide is included in the culture, medium for less than 5 days or more than 100 days. In certain embodiments, a first concentration of an OSM polypeptide is included in the culture medium for a first period of time and a second concentration of an OSM polypeptide is included in the culture medium for a second period of time.

In certain embodiments, an OSM polypeptide is included in the culture medium at a concentration between 1 ng/ml and 100 ng/ml, or between 10 ng/ml and 50 ng/ml, or between 15 ng/ml and 35 ng/ml. In certain embodiments, an OSM polypeptide is included in the culture medium below 1 ng/ml or above 100 ng/ml. As a nonlimiting example, 25 ng/ml an OSM polypeptide may be included in the culture medium for a total of 10 days, although other components may be added, removed, or change concentrations at any point or points during that time.

In certain embodiments, the OSM polypeptide used in the differentiation protocol is an OSM. In certain embodiments, the OSM polypeptide used in the differentiation protocol is a human OSM. In certain embodiments, the OSM polypeptide used in the differentiation protocol is a fragment of an OSM. In certain embodiments, the OSM polypeptide used in the differentiation protocol is an active protein that is at least 95% identical to an OSM.

In certain embodiments, an HGF polypeptide and an EGF polypeptide are included in the culture medium at the same time, although each may also be included without the other at one or more times during the same culture protocol. In certain embodiments, an HGF polypeptide, an EGF polypeptide, and dexamethasone are included in the culture medium at the same time, although each may also be included without the other at one or more times during the same culture protocol. In certain embodiments, an HGF polypeptide, an EGF polypeptide, and an OSM polypeptide are included in the culture medium at the same time, although each may also be included without the other at one or more times during the same culture protocol.

In certain embodiments, the primate pluripotent stem cells may be differentiated into hepatocyte-lineage cells by direct differentiation. Differentiation paradigms for primate pluripotent stem cells traditionally involve the deliberate formation of embryoid bodies, which allows cross-talk between different cell types, which may promote tissue formation in a manner reminiscent of an embryo. However, it is often advantageous to eliminate the need to form embryoid bodies, allowing the differentiation process to be more controlled, and the resulting cell population may be more uniform (see, e.g., WO 01/51616; US 2002/0151053 A1).

In certain embodiments, the culture medium used during the differentiation steps is serum-free. In various embodiments, the culture medium used during the differentiation steps contains less than 0.25% serum, or less than 0.5% serum, or less than 1.0% serum, or less than 2.0% serum, or less than 5.0% serum, or less than 10% serum.

Notwithstanding the advantages of the direct differentiation method, in certain embodiments, the primate pluripotent stem cells may be differentiated into hepatocyte-lineage cells through the formation of aggregates at some point in the differentiation protocol.

In certain embodiments, the differentiating cells are cultured on a substrate. Substrates include, but are not limited to collagen, laminin, fibronectin, vitronectin, hyaluronate poly-L-lysine-coated tissue culture plastic, and Matrigel.

Certain solid surfaces may be used in the culturing of cells. Those solid surfaces include, but are not limited to, standard cell culturing plates such as 6-well, 24-well, 96-well, or 144-well plates. Certain solid surfaces also include, but are not limited to, microcarriers and disks. In certain embodiments, the microcarriers are beads. Beads come in various forms, including but not limited to, Cytodex dextran microcarrier beads with positively charged groups, gelatin/collagen-coated beads, and macroporous microcarrier beads with different porosities. Various beads, including Cytodex dextran microcarrier beads, gelatin-coated beads, and macroporous microcarrier beads are commercially available from, e.g., Sigma-Aldrich, St. Loius, Mo. and/or Solohill Engineering Inc., Ann Arbor, Mich. In certain embodiments, the beads are 90-200 µm in size with a total area of 350-500 cm². In certain embodiments, disks may be used in stirred-tank bioreactors to attach the cells. Disks are commercially available from, e.g., New Brunswick Scientific Co, Inc. (Edison, N.J.). In certain embodiments, the disks are Fibra-cel disks (New Brunswick Scientific Co.), which are polyester/polypropylene disks. A gram of Fibra-cel disks provides a surface area of 1200 cm².

The solid surface may be made of a variety of substances including, but not limited to, glass or plastic. Plastics include, but are not limited to, polystyrene, polyvinylchloride, polycarbonate, polytetrafluorethylene, melinex, and thermanox. In certain embodiments, the solid surface is three-dimensional in shape. Exemplary three-dimensional solid surfaces are described, e.g., in US20050031598.

In certain embodiments, the cells are in a single-cell suspension. The single-cell suspension may be cultured in various bioreactors including, but not limited to, spinner flasks, shaker flasks, and fermentors. Exemplary fermentors include, but are not limited to, Celligen Plus (New Brunswick Scientific Co, Inc., Edison, N.J.), and the Stirred-Tank Reactor (STR; Applikon Inc., Foster City, Calif.). In certain embodiments, the bioreactors may be continuously perfused with media or may be used in a fed-batch mode. Bioreactors come in various sizes, for example, 2.2 L, 5 L, 7.5 L, 14 L and 20 L.

Enriching and Expanding Hepatocyte-Lineage Cells

In certain embodiments, the invention provides methods for obtaining hepatocyte-lineage cell populations without an enrichment step. However, the addition of one or more enrichment steps may produce a higher purity hepatocyte-lineage cell population. Thus, certain methods may include steps for enriching and/or expanding hepatocyte-lineage cells. Various methods for enriching specific cell types are known in the art and include, but are not limited to, mechanical separation, density separation; cell sorting, magnetic sorting, and genetic selection techniques. For a discussion of cell separation, see, e.g., Freshney, Culture of Animal Cells, Wiley-Liss, New York, 2000—Chapter 14. Certain exemplary methods of enriching and/or expanding hepatocyte-lineage cells are discussed below.

Density Gradients

In certain embodiments, hepatocyte-lineage cells are enriched by density gradient separation using a density gradient medium. Exemplary density gradient mediums include, but are not limited to, Percoll (see, e.g., Xu et al., Circ. Res. 91(6):501-08, 2002), Ficoll (Pharmacia), metrizamide (Nygaard), RediGrad (GE Healthcare) and dextran.

Cell Sorting Techniques

Many cell sorting techniques are available for sorting hepatocyte-lineage cells from non-hepatocyte-lineage cells. Exemplary cell sorting techniques include, but are not limited to, negative immunoselection and positive immunoselection.

Immunoselection is a generic term that encompasses a variety of techniques in which the specificity of a selection system is conferred by an antibody or other selective binding agent. Exemplary selective binding agents include, but are not limited to, lectin and hapten. Specificity may be achieved, e.g., by binding an antibody or selective binding agent to a specific cell surface antigen. Immunoselection includes two general techniques. Negative immunoselection involves the elimination of a specific subpopulation of components from a heterogeneous population, e.g., elimination of non-hepatocyte-lineage cells from hepatocyte-lineage cells. Positive immunoselection involves the direct selection and recovery of a specific subpopulation of components in a heterogeneous population, e.g., selection and recovery of hepatocyte-lineage cells from other, non-hepatocyte-lineage cells. Various types of immunoselection may be used in the practice of the present invention, including, but not limited to, flow cytometry (FACS), immunomagnetic techniques, antibody columns, immunoprecipitation, and immunopanning.

Characterization of ES-Differentiated Hepatocyte-Lineage Cells

Hepatocyte-lineage cells can be characterized according to certain phenotypic criteria. Certain criteria include, but are not limited to, the detection and/or quantitation of expressed cell markers, enzymatic activity, and the characterization of morphological features and intercellular signaling.

Certain hepatocyte-lineage cells have features characteristic of hepatocytes. Exemplary features characteristic of hepatocytes include, but are not limited to, a polygonal cell shape, a binucleate phenotype, the presence of rough endoplasmic reticulum, the presence of Golgi-endoplasmic reticulum lysosome complex, the presence of peroxisomes and glycogen granules, and the ability to form tight intercellular junctions resulting in creation of bile canalicular spaces.

An exemplary method of determining whether a population of cells has features characteristic of hepatocytes follows. A micrograph of the cell population can be coded, e.g., by determining the presence or absence of one or more features characteristic of hepatocytes. As a positive control, a micrograph of adult or fetal hepatocytes is similarly coded. Micrographs of non-hepatocyte cells, such as fibroblasts or RPE (Retinal pigment epithelial) cells, may be used as negative controls. The results of the coding of the cell population, positive control, and negative control are then compared to determine whether the cell population has features characteristic of hepatocytes. In certain embodiments, hepatocyte-lineage cells have at least two, at least three, at least four, at least five, or at least six features characteristic of hepatocytes.

Hepatocyte-lineage cells can also be characterized, e.g., according to whether they express certain markers characteristic of hepatocytes. Certain markers are useful in distinguishing liver progenitors, hepatocytes, and biliary epithelium. Certain exemplary markers that may be used to distinguish those cell types are shown in Table 1 (see, e.g., p 35 of Sell & Zoran, Liver Stem Cells, R. G. Landes Co., TX, 1997; and Grisham et al., p 242 of Stem Cells, Academic Press, 1997).

ers may be detected at the mRNA level by various techniques, including but not limited to, Northern blot analysis, dot-blot hybridization analysis, and reverse transcriptase initiated polymerase chain reaction (RT-PCR). See, e.g., U.S. Pat. No. 5,843,780. Sequence-specific primers used in various techniques may be designed using publicly available sequence data (e.g., GenBank; www.ncbi.nlm.nih.gov). Expression of tissue-specific gene products is considered "detectable" in a particular assay if performance of the assay on cell samples according to standard procedures in a typical controlled experiment results in clearly discernable hybridization or amplification product.

In certain embodiments, the expression level of one or more markers in hepatocyte-lineage cells is compared to the expression level of those markers in other cells. Exemplary positive controls for expression of certain markers include, but are not limited to, adult hepatocytes, fetal hepatocytes, and certain established hepatocyte cell lines. Certain established cell lines and long-term hepatocyte cell cultures, however, may be metabolically altered, and therefore may fail to express certain markers characteristic of hepatocytes and/or may inappropriately express certain markers whose absence

TABLE 1

Hepatocyte Cell Markers

|  | early progenitors | hepatocytes | biliary epithelium |  | Early progenitors | hepatocytes | biliary epithelium |
|---|---|---|---|---|---|---|---|
| albumin | + | + | − | OC.1 | − | − | + |
| α$_1$-antitrypsin | + | + | − | OC.2 | + | − | + |
| AFP | + | fetal & postnatal | − | OC.3 | + | − | + |
| CEA | − | − | + (?) | BD.1 | + | − | + |
| γ-glutamyl tranpeptidase | + | fetal | + | A6 | + | − | + |
| GST-P | + | fetal | + | HBD.1 | + | + | + |
| glucose-6-phosphatase | + | + | − | H.2 | − | + | − |
| catalase | − | + | − | H.4 | − | + | − |
| M2-PK | + | fetal | + | H-4 | ? | + | − |
| L-PK | − | + | fetal | H-6 | − | + | − |
| p450 mono-oxygenase | + | + | − | HES$_6$ | − | + | − |
| P-glycoprotein | ? | canaliculi | − | RL16/79 | − | postnatal | − |
| CK7 | − | − | + | RL23/36 | − | + | − |
| CK8 | + | + | + | BPC$_5$ | + | − | − |
| CK14 | + | − | − | Vimentin | − | − | fetal |
| CK18 | + | + | + | HepPar1 | + | + | − |
| CK19 | −(+) | − | + | Cell-CAM 105 | + | + | − |
| CKX | + | − | + | DPP IV | + | canaliculi | + |
| BDS$_7$ | + | − | + | lectin binding sites | + | − | + |
| OV1 | + | − | + | blood group antigens | + | − | + |
| OV6 | − | − | + |  |  |  |  |

In certain embodiments, hepatocyte differentiation requires the transcription factor HNF-4a (see, e.g., Li et al., Genes Dev. 14:464, 2000). Certain markers independent of HNF-4a expression include, but are not limited to, α1-antitrypsin, AFP, apoE, glucokinase, insulin growth factors 1 and 2, IGF-1 receptor, insulin receptor, and leptin. Certain markers dependent on HNF-4α expression include, but are not limited to, albumin, apoAI, apoAII, apoB, apoCIII, apoCII, aldolase B, phenylalanine hydroxylase, L-type fatty acid binding protein, transferrin, retinol binding protein, and erythropoietin (EPO). Exemplary markers include those presented in the Examples and Figures.

In certain embodiments, hepatocyte-lineage cell markers are detected at the protein level, e.g., by immunohistochemistry. In certain embodiments, hepatocyte-lineage cell markis characteristic of hepatocytes. Exemplary negative controls include, but are not limited to, cells of a non-hepatocyte lineage, such as an adult fibroblasts or RPE cells, as noted above. Certain primate pluripotent cells may be positive for certain markers discussed above and negative for certain other markers discussed above.

Certain tissue-specific markers may be detected using suitable immunological techniques. Such techniques include, but are not limited to, flow immunocytometry, affinity adsorption of cell-surface markers, immunocytochemistry for intracellular or cell-surface markers, Western blots, and enzyme-linked immunoassays. Certain antibodies that detect hepatocyte markers include but are not limited to, antibodies to albumin (Chemicon, cat. no. AB3391; R&D Systems, cat no. MAB1455); alpha-antitrypsin (Chemicon, cat. nos. AB3535 and AB3387; R&D Systems, cat no. MAB 1261); AFP (Chemicon, cat. no. AB3398; R&D Systems, cat nos. AF1369 and MAB 1369); HNF4 alpha (R&D Systems); HNF3 beta (Chemicon, cat. no. AB4125); Cytochrome P450 CYP3A4 (Chemicon, cat nos. AB1254 and AB1278); Cytochrome P450 CYP2D6 (Chemicon, cat nos. AB1251 and AB1273); Cytochrome P450 CYP2C9 and CYP2C19 (Chemicon, cat nos. AB1269).

In certain embodiments, cells can be characterized according to whether they display certain enzymatic activities characteristic of hepatocyte cells. Certain exemplary enzymatic activities characteristic of hepatocyte cells include, but are not limited to, glucose-6-phosphatase activity (see, e.g., Bublitz, Mol Cell Biochem. 108:141, 1991; Yasmineh et al., Clin. Biochem. 25:109, 1992; and Ockerman, Clin. Chim. Acta 17:201, 1968); alkaline phosphatase (ALP) activity, and 5-nucleotidase (5'-Nase) activity (see, e.g., Shiojiri, J. Embryol. Exp. Morph. 62:139, 1981). In addition, certain laboratories offer assays for liver enzyme activity as a commercial service, for example, MDS Pharma Services (www.mdsps.com/drugsafety/ToxInVitro.htm), Covance (www.covance.com/metabolism/svc.inv.php), Becton Dickinson (www.bdbiosciences.com/discovery_labware/gentest/products/pdf/postindx/shtml), In Vitro Technologies (www.invitrotech.com/metabolizing_enzymes.cfm), and Xenotech (www.xenotechllc.com/products/products_immortalized_human.asp).

In certain embodiments, hepatocyte-lineage cells express cytochrome p450. Cytochrome p450 is a catalytic component of the mono-oxygenase system. Cytochrome p450 is a family of hemoproteins responsible for the oxidative metabolism of certain xenobiotics (administered drugs), as well as certain endogenous compounds. Different cytochromes often have characteristic and overlapping substrate specificity. Much of the biotransforming ability of cytochrome p450 is attributable to cytochromes 1A2, 2A6, 2B6, 3A4, 2C9-11, 2D6, and 2E1 (see, e.g., Gomes-Lechon et al., pp 129-153 in In vitro Methods in Pharmaceutical Research, Academic Press, 1997).

Various assays are known in the art for measuring cytochrome p450 enzyme activity. An exemplary assay involves contacting cells with a non-fluorescent substrate that is convertible to a fluorescent product by p450 activity, and then analyzing the cells by fluorescence-activated cell counting (see, e.g., U.S. Pat. No. 5,869,243). In certain embodiments of that assay, the cells are washed, and then incubated with a solution of 10 μM 5,6-methoxycarbonylfluorescein (Molecular Probes, Eugene Oreg.) for 15 minutes at 37° C. in the dark. The cells are washed, trypsinized from the culture plates, and then analyzed for fluorescence emission at ~520-560 nm. Another exemplary p450 enzyme activity assay uses HPLC and is described, e.g., in Example 3.

In certain embodiments, a cell is said to have a specific enzyme activity if the level of activity in the cell is at least 10-fold above the level of activity in a control cell. One skilled in the art can select a suitable control cell. For cytochrome p450 assays, suitable control cells include, but are not limited to, fibroblasts. In certain embodiments, the level of enzyme activity in a cell is at least 100-fold or at least 1000-fold, above that level of enzyme activity in a control cell. In certain embodiments, hepatocyte-lineage cells have enzyme activity levels that are similar to or within 2-fold or within 10-fold of the level of enzyme activity in adult hepatocyte cells. In certain embodiments, hepatocyte-lineage cells have enzyme activity levels that are similar to or within 2-fold or within 10-fold of the level of enzyme activity in a fetal hepatocyte.

The expression of cytochrome p450 protein can also be measured, e.g., using Western blots. The expression of cytochrome p450 mRNA can also be measured, e.g., using Northern blots and/or RT-PCR. See, e.g., Borlakoglu et al., Int. J. Biochem. 25:1659, 1993. Certain enzymatic activities of the p450 system can also be measured. In certain embodiments, such activities include, but are not limited to, 7-ethoxycoumarin O-de-ethylase activity, aloxyresorufin O-de-alkylase activity, coumarin 7-hydroxylase activity, p-nitrophenol hydroxylase activity, testosterone hydroxylation activity, UDP-glucuronyltransferase activity, and glutathione S-transferase activity. In certain embodiments, the level of activity of one or more enzymes of the p450 system in hepatocyte -lineage cells is compared to the level of activity of the same enzymes in adult hepatocytes or fetal hepatocytes. Exemplary levels of activity of certain enzymes of the p450 system in primary adult hepatocytes is shown in Table 2. Phase I and Phase II refer to the stages of transformation of molecules during drug metabolism.

TABLE 2

Drug Metabolizing Activities in 24 hour Primary Cultured Human Hepatocytes

|  | Isozyme | Reaction | Activity | |
|---|---|---|---|---|
| Phase I | P450† |  | 65 ± 8 | (n = 10) |
|  | NADPH-Cc‡ | Cytochrome c oxidation | 23 ± 2 | (n = 10) |
|  | CYP1A1/2d§ | Aryl hydrocarbon hydroxylation | 2.93 ± 0.99 | (n = 7) |
|  |  | 7-Ethoxyresorufin O-de-ethylation | 3.09 ± 2.52 | (n = 14) |
|  | CYP2A6§ | Coumarin 7-hydroxylation | 137 ± 42 | (n = 6) |
|  | CYP2B6§ | 7-Pentoxyresorufin O-depentylation | 3.28 ± 1.76 | (n = 10) |
|  |  | 7-Benzoxyresorufin O-debenzylation | 1.38 ± 0.33 | (n = 5) |
|  | CYP2C9§ | 4'-Diclofenac hydroxylation | 317 ± 73 | (n = 9) |
|  | CYP2E1§ | p-Nitrophenol hydroxylation | 89 ± 42 | (n = 6) |
|  |  | Chlorzoxazone 6-hydroxylation | 27 ± 3 | (n = 3) |
|  | CYP3A3-5§ | Testosterone 6β-hydroxylation | 195 ± 122 | (n = 7) |
|  |  | Testosterone 2β-hydroxylation | 61 ± 16 | (n = 7) |
|  |  | Testosterone 15β-hydroxylation | 12.4 ± 8.6 | (n = 7) |
| Phase II | mEH§ | Benzo(a)pyrene 7,8-oxide hydration | 180 ± 72 | (n = 10) |
|  | UDPG-t‡ | 4-Methylumbelliferone conjugation | 3.6 ± 0.4 | (n = 5) |
|  | GSH-t‡ | 1-Chloro-2,4-dinitrobenzene conjugation | 301 ± 112 | (n = 8) |

*Mean ± s.d. enzymatic activity determined in 24-h cultured human hepatocytes.
†Cytochrome P450 content is expressed as picomoles per milligram of cellular protein.
‡NADPH-C, UDPG-t and GSH-t activities are expressed as nanomoles per milligram per minute.
§CYP enzymatic activities are expressed as picomoles per milligram per minute.

Assays are also available for certain enzymes involved in the conjugation, metabolism, and/or detoxification of small molecule drugs. For example, cells can be characterized by the ability to conjugate bilirubin, bile acids, and/or small molecule drugs, e.g., for excretion through the urinary or biliary tract. In certain exemplary assays, cells are contacted with a suitable substrate, incubated for a suitable period, and then the medium is analyzed (e.g., by gas chromatogaphy/mass spectrometry (GCMS) or other suitable technique) to determine whether a conjugation product has been formed. Certain drug metabolizing enzyme activities include, but are not limited to, de-ethylation, dealkylation, hydroxylation, demethylation, oxidation, glucuroconjugation, sulfoconjugation, glutathione conjugation, and N-acetyl transferase activity (see, e.g., A. Guillouzo, pp 411-431 in In vitro Methods in Pharmaceutical Research, Academic Press, 1997). Exemplary assays include, but are not limited to, phenacetin de-ethylation, procainamide N-acetylation, paracetamol sulfoconjugation, and paracetamol glucuronidation (see, e.g., Chesne et al., pp 343-350 in Liver Cells and Drugs, A. Guillouzo ed. John Libbey Eurotext, London, 1988).

In certain embodiments, hepatocyte-lineage cells are evaluated by their ability to store glycogen. An exemplary assay uses Periodic Acid Schiff (PAS) stain, which does not react with mono- and disaccharides, but stains long-chain polymers such as glycogen and dextran. PAS assays provide, in certain embodiments, quantitative estimates of complex carbohydrate levels as well as levels of soluble and membrane-bound carbohydrate compounds. See, e.g., Kirkeby et al., Biochem. Biophys. Meth. 24:225, 1992, which describes a quantitative PAS assay of carbohydrate compounds and detergents; and van der Laarse et al., Biotech Histochem. 67:303, 1992, which describes a microdensitometric histochemical assay for glycogen using the PAS reaction. Cells are considered to store glycogen if the cells have at least a 2-fold higher level of staining in a PAS assay than a control cell. In certain embodiments, a hepatocyte-lineage cell has at least a 5-fold or at least a 10-fold level of staining when compared to a control cell. One skilled in the art can select suitable control cells, for example, cells that do not store glycogen. Suitable control cells include, but are not limited to, fibroblasts.

In certain embodiments, hepatocyte-lineage cells are susceptible under appropriate circumstances to pathogenic agents that are tropic for primate liver cells. Such agents include, but are not limited to, hepatitis A, B, C, and delta, Epstein-Barr virus (EBV), cytomegalovirus (CMV), tuberculosis, and malaria. Infectivity by hepatitis B can be determined, in certain embodiments, by combining hepatocyte-lineage cells with a source of infectious hepatitis B particles (such as serum from an HBV carrier). The hepatocyte-lineage cells can then be tested for synthesis of viral core antigen (HBcAg) by immunohistochemistry and/or RT-PCR.

In certain embodiments, hepatocyte-lineage cells are essentially free of other cell types that typically contaminate primary hepatocyte cultures isolated from adult or fetal liver tissue. Certain markers may be useful in determining whether other cell types are present in a population. Markers characteristic of sinusoidal endothelial cells include, but are not limited to, von Willebrand factor, CD4, CD14, and CD32. Markers characteristic of bile duct epithelial cells include, but are not limited to, cytokeratin-7, cytokeratin-19, and γ-glutamyl transpeptidase. Markers characteristic of stellate cells include, but are not limited to, α-smooth muscle actin (α-SMA), vimentin, synaptophysin, glial fibrillary acidic protein (GFAP), neural-cell adhesion molecule (N-CAM), and the presence of lipid droplets (detectable by autofluorescence or staining by oil red O). Markers characteristic of Kupffer cells include, but are not limited to, CD68, certain lectins, and certain markers for cells of the macrophage lineage (including, but not limited to, HLA Class II, and mediators of phagocytosis). A population of hepatocyte-lineage cells are considered to be essentially free of other cell types when less than 0.1% of the population bears markers of an undesired cell type, as determined by immunostaining and fluorescence-activated quantitation.

In certain embodiments, hepatocyte-lineage cells are characterized as being of a particular stage by their features and/or marker expression patterns. In various embodiments, a population of hepatocyte-lineage cells comprises at least 40%, at least 60%, at least 80%, at least 90%, at least 95%, or at least 98% cells with the same features and/or marker expression patterns according to a chosen assay.

Hepatocyte-Lineage Cells Having Certain Genetic Alterations

Hepatocyte-lineage cells containing one or more genetic alterations can be made by genetic engineering of the cells either before or after differentiation (see, e.g., U.S. Publication No. 2002/0168766 A1). For example, cells can be modified in such a way as to increase their replication potential by genetically altering the cells to express telomerase reverse transcriptase. Such modifications can be made, e.g., before or after the cells progress to restricted developmental lineage cells or terminally differentiated cells (see, e.g., U.S. Publication No. 2003/0022367 A1).

In certain embodiments, hepatocyte lineage cells can be genetically altered in order to enhance their ability to be involved in tissue regeneration and/or to deliver a therapeutic gene to a site of administration. As a nonlimiting example, a vector may be designed to express the desired gene, by linking its coding sequence to a promoter that is either pan-specific or specifically active in the differentiated cell type. In certain embodiments, expression of particular genes at the site of hepatocyte-lineage cell administration may facilitate adoption of the functional hepatocyte phenotype, enhance the beneficial effect of the administered cell, and/or increase proliferation and/or activity of host cells neighboring the treatment site.

In certain embodiments, it is desirable to genetically alter non-human hepatocyte-lineage cells such that expression of one or more antigens is reduced or eliminated, which may reduce the immunogenecity of the cells. Such a modification could be useful, for example, in xenotransplantation of non-human hepatocyte-lineage cells into a human.

Uses of Hepatocyte-Lineage Cells

The hepatocyte-lineage cells described herein may, in certain embodiments, be used for a number of important research, development, and/or commercial purposes.

Screening

In certain embodiments, hepatocyte-lineage cells can be used to screen for factors (such as solvents, small molecule drugs, peptides, oligonucleotides) and/or environmental conditions (such as culture conditions and manipulation) that affect the characteristics of such cells and their progeny.

In certain embodiments, primate pluripotent stem cells are used to screen for factors that promote maturation into hepatocyte-lineage cells and/or promote proliferation and maintenance of hepatocyte-lineage cells in long-term culture. In an exemplary method, candidate maturation factors or growth factors are tested by adding them to primate pluripotent stem cells in different wells, and any phenotypic change that results is then determined.

Certain other screening methods relate to testing pharmaceutical compounds for their effect on hepatocyte tissue maintenance or repair. In certain embodiments, pharmaceutical compounds are screened for pharmacological effect on the hepatocyte-lineage cells. In certain embodiments, pharmaceutical compounds are screened using hepatocyte cells to determine whether compounds designed to have effects elsewhere have unintended side effects on hepatocyte-lineage cells.

Certain methods of screening are known in the art and are discussed, e.g., in *In vitro Methods in Pharmaceutical Research*, Academic Press, 1997; and in U.S. Pat. No. 5,030,015. In certain embodiments, assessment of the activity of candidate pharmaceutical compounds involves combining hepatocyte-lineage cells with a candidate compound, either alone or in combination with other compounds. An investigator may then determine whether the cells have undergone any change in morphology, marker expression, or functional activity that may be attributable to the compound. Untreated hepatocyte lineage cells and/or hepatocyte lineage cells treated with a compound predicted to be inert may be used as controls.

Cytotoxicity can be determined, in various embodiments, by the effect on cell viability, survival, morphology, and/or the expression of certain markers and receptors. In addition, effects of a drug on chromosomal DNA can be determined, e.g., by measuring DNA synthesis or repair. [$^3$H]-thymidine or BrdU incorporation, especially at unscheduled times in the cell cycle, or above the level required for cell replication, may be consistent with a drug effect. Unwanted drug effects can also include unusual rates of sister chromatid exchange, which may be determined, e.g., by metaphase spread. See, e.g., A. Vickers, pp 375-410 in *In vitro Methods in Pharmaceutical Research*, Academic Press, 1997.

Drug effects on cell function can be assessed, e.g., using standard assays to observe phenotype and/or activity of hepatocyte-lineage cells. Such activities include, but are not limited to, marker expression, receptor binding, and enzymatic activity. Certain activities that can be assayed in order to evaluate hepatotoxicity include, but are not limited to, synthesis and/or secretion of albumin, cholesterol, and/or lipoproteins; transport of conjugated bile acids and/or bilirubin; ureagenesis; cytochrome p450 levels and/or activities; glutathione levels; release of α-glutathione s-transferase; ATP, ADP, and/or AMP metabolism; intracellular $K^+$ and/or $Ca^{2+}$ concentrations; release of nuclear matrix proteins and/or oligonucleosomes; and induction of apoptosis (indicated by, e.g., cell rounding, condensation of chromatin, and/or nuclear fragmentation). Where an effect is observed, the concentration of the compound can be titrated to determine the median effective dose ($ED_{50}$).

Exemplary hepatocyte-lineage cell enzyme activities that may be beneficial for drug screening are shown in Table 3. Exemplary catalysis rates for each enzyme are also shown.

TABLE 3

Desirable Enzyme Specifications for Drug Screening

| Enzyme | Substrate | Catalysis Rate | |
|---|---|---|---|
| CYP3A4 | Testosterone | 66 (5-286) | pmol/min/$10^6$ cells |
| CYP2D6 | Dextromethorphan | 23 (2-72) | pmol/min/$10^6$ cells |
| CYP2C9 | Tolbutamide | 16 (3-58) | pmol/min/$10^6$ cells |
| CYP1A2 | Ethoxyresorufin | 0.13 (0-30.2) | pmol/min/$10^6$ cells |
| UDP-GT | Umbelliperone | | |
| Sulfo-transferases | Umbelliperone | | |

Certain Exemplary Therapeutics

In certain embodiments, the hepatocyte-lineage cells discussed herein can be used to enhance tissue maintenance or repair of liver tissue for any perceived need, including, but not limited to, liver tissue having an inborn error in metabolic function, liver tissue damaged by the effect of a disease condition, liver tissue damaged by the effect of a toxin, and/or liver tissue damaged by trauma.

Animal Testing

To determine the suitability of hepatocyte-lineage cell compositions for therapeutic administration, hepatocyte-lineage cells can first be tested in a suitable animal model. In such a model, hepatocyte-lineage cells may be assessed for their ability to survive and maintain their phenotype in vivo. Cell compositions are administered, e.g., to immunodeficient animals (including, but not limited to, nude mice and animals rendered immunodeficient chemically and/or by irradiation). Tissues may be harvested after a period of regrowth, and assessed as to whether pluripotent stem cell-derived hepatocyte-lineage cells are still present.

In order to detect surviving hepatocyte-lineage cells after administration to an animal model, the hepatocyte-lineage cells can, in certain embodiments, be labeled prior to administration. In certain embodiments, the hepatocyte-lineage cells are modified to express a detectable label, e.g., green fluorescent protein or β-galactosidase. One skilled in the art can select an appropriate detectable label for a given application. In certain embodiments, hepatocyte-lineage cells are labeled prior to administration, e.g., with BrdU and/or [$^3$H] thymidine. In certain embodiments, hepatocyte-lineage cells are not labeled, but instead are detected after administration by detection of a constitutive cell marker. Detection of a constitutive cell marker can include, for example, specific detection of a human antigen expressed by the hepatocyte-lineage cells, e.g., using a human-specific antibody. In certain embodiments, hepatocyte-lineage cell mRNA can be detected, e.g., by RT-PCR analysis using primers and hybridization conditions that cause amplification to be specific for human polynucleotides. Specific primers can be designed, e.g., using publicly available sequence data. For discussions on determining the fate of hepatocyte-lineage cells in animal models, see, e.g., Grompe et al., Sem. Liver Dis. 19:7, 1999; Peeters et al., Hepatology 25:884, 1997; and Ohashi et al., Nature Med. 6:327, 2000.

In certain embodiments, hepatocyte-lineage cells are assessed for their ability to restore liver function in an animal lacking full liver function. Certain exemplary assays can be found in the literature. For example, Braun et al., Nature Med. 6:320, 2000, discuss a model for toxin-induced liver disease in mice transgenic for the HSV tk gene. Rhim et al., Proc. Natl. Acad. Sci. USA 92:4942, 1995, and Lieber et al., Proc. Natl. Acad. Sci. USA 92:6210, 1995, discuss models for liver disease that express urokinase. Mignon et al., Nature Med. 4:1185, 1998, discuss liver disease induced by antibodies to the cell-surface marker Fas. Overturf et al., Human Gene Ther. 9:295, 1998, have developed a model for Hereditary Tyrosinemia Type I in mice using targeted disruption of the Fah gene. Those animals can be rescued from the deficiency by administering 2-(2-nitro-4-fluoro-methyl-benzyol)-1,3-cyclohexanedione (NTBC), but they develop liver disease when NTBC is withdrawn. Acute liver disease can also be modeled by 90% hepatectomy (see, e.g., Kobayashi et al., Science 287:1258, 2000), and/or by treating animals with a hepatotoxin such as galactosamine, CC14, or thioacetamide. Chronic liver diseases, including but not limited to cirrhosis, can be modeled, e.g., by treating animals with a sub-lethal dose of a hepatotoxin long enough to induce fibrosis (see, e.g., Rudolph et al., Science 287:1253, 2000).

In certain embodiments, to assess the ability of hepatocyte-lineage cells to reconstitute liver function, hepatocyte-lineage cells are administered to animals, and the survival of the animals is monitored over a period of time. In certain embodiments, the progress of the condition is also monitored during that time. In certain embodiments, hepatic function is also monitored during that time, e.g., by detecting certain markers expressed in liver tissue, by assaying cytochrome p450 activity, and/or by measuring certain blood indicators, such as alkaline phosphatase activity, bilirubin conjugation, and prothrombin time. The results of such experiments can then be used to optimize a treatment regimen using hepatocyte-lineage cells.

Therapeutic Use in Humans

In certain embodiments, hepatocyte-lineage cells can be used for tissue reconstitution and/or regeneration in a human patient or other subject in need of such treatment. The cells are administered in a manner that permits them to graft and/or migrate to the intended tissue site and reconstitute and/or regenerate the functionally deficient area. Certain special devices are available that are adapted for administering cells capable of reconstituting liver function directly to the liver at the desired location.

Use in a Liver Assist Device

In certain embodiments, hepatocyte-lineage cells can be used in a bioartificial liver device. In certain embodiments, hepatocyte-lineage cells can be encapsulated for use either in vivo or in vitro. Certain encapsulation methods are described, e.g., in Cell Encapsulation Technology and Therapeutics, Kuhtreiber et al. eds., Birkhauser, Boston Mass., 1999.

Bioartificial organs for clinical use can be designed to support an individual with impaired liver function as a part of long-term therapy and/or to bridge the time between a fulminant hepatic failure and hepatic reconstitution or liver transplant. Bioartificial liver devices are reviewed, e.g., by Macdonald et al., pp. 252-286 of "Cell Encapsulation Technology and Therapeutics", op cit. Certain exemplary bioartificial liver devices are described, e.g., in U.S. Pat. Nos. 5,290,684; 5,624,840; 5,837,234; 5,853,717; and 5,935,849. Suspension-type bioartificial livers devices comprise, in certain embodiments, cells suspended in plate dialysers, cells microencapsulated in a suitable substrate, and/or cells attached to microcarrier beads coated with extracellular matrix. Bioartificial liver devices may also comprise cells placed on a solid support in a packed bed, cells in a multiplate flat bed, cells on a microchannel screen, and/or cells surrounding hollow fiber capillaries. Bioartificial liver devices typically comprise an inlet and outlet through which the subject's blood is passed. In certain embodiments, a bioartificial liver device further comprises a separate set of ports for supplying nutrients to the cells.

In certain embodiments, hepatocyte-lineage cells are plated into the bioartificial liver device on a suitable substrate, such as a matrix of Matrigel and/or collagen. The efficacy of the device can be assessed, in certain embodiments, by comparing the composition of blood before passing through the device to the composition of blood after passing through the device. Such comparison can be made, e.g., by comparing the presence and/or absence of certain metabolites and/or proteins in the blood before and after passing through the device.

Certain devices can be used to detoxify a fluid. Fluids that may be detoxified include, for example, blood. In certain embodiments, the fluid comes into contact with hepatocyte-lineage cells in the device under conditions that permit the cells to remove and/or modify certain components of the fluid. Exemplary components include, but are not limited to, toxins, metabolites, small molecules (including natural and synthetic small molecules and pharmaceutical compounds), bilirubin, bile acids, urea, heme, lipoprotein, carbohydrates, transferrin, hemopexin, asialoglycoproteins, and hormones (including but not limited to, insulin and glucagon). In certain embodiments, a device can be used to enrich the fluid with synthesized proteins. Exemplary synthesized proteins include, but are not limited to, albumin, acute phase reactants, and unloaded carrier proteins. In certain embodiments, a device can be optimized so that it performs a variety of these functions, i.e., so that it performs two or more of removing components from a fluid, modifying components in a fluid, and enriching a fluid with synthesized proteins. In the context of therapeutic care, the device may process blood flowing from a patient with some form of hepatocyte failure, including impaired liver function, and then the blood is returned to the patient.

Use for Transplantation

Hepatocyte-lineage cells may also be suitable for direct administration to human subjects, including human subjects with impaired liver function. In certain embodiments, specific hepatocyte-lineage cell populations are chosen according to their expression of certain enzymes, expression of certain markers and/or efficacy in animal models. In certain embodiments, the hepatocyte-lineage cells can be administered at any site that has adequate access to the circulation, including but not limited to, administration into the abdominal cavity. In certain embodiments, it is advantageous for the cells to have access to the biliary tract; e.g., if the hepatocyte-lineage cells are being administered to carry out certain metabolic and/or detoxification functions. Accordingly, the cells may be administered near the liver (e.g., in the treatment of chronic liver disease) and/or the spleen (e.g., in the treatment of fulminant hepatic failure). In certain embodiments, hepatocyte-lineage cells are administered into the hepatic circulation, e.g., through the hepatic artery and/or through the portal vein, by infusion through an in-dwelling catheter. A catheter in the portal vein can be manipulated so that the cells flow principally into the spleen, or the liver, or a combination of both. In certain embodiments, hepatocyte-lineage cells are administered by placing a bolus in a cavity near the target organ, typically in an excipient or matrix that will keep the bolus in place. In certain embodiments, hepatocyte-lineage cells are injected directly into a lobe of the liver and/or into the spleen.

Hepatocyte-lineage cells can, in certain embodiments, be used for therapy in any subject needing restoration or augmentation of hepatic function. Exemplary conditions that may result in such a need include, but are not limited to, fulminant hepatic failure due to any cause, viral hepatitis, drug-induced liver injury, cirrhosis, inherited hepatic insufficiency (including, but not limited to, Wilson's disease, Gilbert's syndrome, and α1-antitrypsin deficiency), hepatobiliary carcinoma, autoimmune liver disease (including but not limited to, autoimmune chronic hepatitis and primary biliary cirrhosis), and other conditions that results in impaired hepatic function. One skilled in the art can choose an appropriate dose of hepatocyte-lineage cells and an appropriate route of administration. In various embodiments, hepatocyte-lineage cells are administered at a dose of between about $10^9$ and $10^{12}$ cells, or between about $5 \times 10^9$ and $5 \times 10^{10}$ cells. The dose may be adjusted to take into account the body weight of the subject, the nature and/or severity of the affliction, and/or the replicative capacity of the administered cells. In various embodiments, a course of treatment involves one dose, at least two doses, at least five doses, or at least ten doses of hepatocyte-lineage cells. In various embodiments, a course of treatment involves daily, weekly, or monthly administrations of hepatocyte-lineage cells.

Distribution for Commercial, Therapeutic, and Research Purposes

The hepatocyte-lineage cells of this invention can be supplied in the form of a pharmaceutical composition, comprising an isotonic excipient prepared under sufficiently sterile conditions for human administration. To reduce the risk of cell death upon engraftment, the cells may be treated by heat shock or cultured with ~0.5 U/mL erythropoietin for ~24 hours before administration.

For a discussion of medicinal formulation, see, e.g., *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. One skilled in the art can choose an appropriate excipient and any accompanying elements of the composition according to the route and device selected for administration. In certain embodiments, the composition may comprise and/or be accompanied with one or more other ingredients that facilitate the engraftment and/or functional mobilization of the hepatocyte-lineage cells. Exemplary other ingredients include, but are not limited to, matrix proteins that support and/or promote adhesion of the hepatocyte-lineage cells, and complementary cell types (including, but not limited to, endothelial cells).

A reagent system is also provided, comprising a set or combination of cells. Such cell sets include, but are not limited to, any combination of two or more cell populations described herein. Such cell populations include, but are not limited to, primate pluripotent stem cells, hepatocyte-lineage cells of any stage (including, but not limited to, hepatocyte precursors and mature hepatocytes), and other differentiated cell types. In certain embodiments, the cell set comprises two or more populations of cells having the same genome. In certain embodiments, the cell sets comprise two or more populations of cells having the same genome but for one or more allotypic differences. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of hepatocyte-lineage cell function to improve a disease condition or abnormality of the liver.

Expression Libraries, Specific Antibody, and Genomic Analysis

In certain embodiments, hepatocyte-lineage cells can be used to prepare a cDNA library that is substantially uncontaminated by cDNA from mRNAs present in other cell types and substantially absent in hepatocyte-lineage cells. For example, hepatocyte-lineage cells are collected by centrifugation at 1000 rpm for 5 minutes, and mRNA is prepared and reverse transcribed. Expression patterns of the hepatocyte-lineage cells can be compared with other cell types by microarray analysis. Microarray analysis is discussed, e.g., in Fritz et al *Science* 288:316, 2000; and "Microarray Biochip Technology", L Shi, www.Gene-Chips.com.

Hepatocyte-lineage cells may be used to identify expression patterns that are characteristic of hepatocyte-lineage cells. Those expression patterns may assist, e.g., in directing the differentiation pathway of those cells. Those expression patterns may also assist, e.g., in detecting characteristic differences between hepatocytes of different allotypes and/or hepatocytes associated with certain conditions. Expression patterns of the hepatocyte-lineage cells can also be compared with certain control cell lines, such as primate pluripotent stem cells, using any suitable technique, including but not limited to immunoassay, immunohistochemistry, differential display, and microarray analysis.

Hepatocyte-lineage cells can also be used to prepare antibodies that are specific for markers of hepatocyte-lineage cells. Polyclonal antibodies can be prepared by injecting a vertebrate animal with hepatocyte-lineage cells in an immunogenic form. Monoclonal antibodies can also be prepared. Production of monoclonal antibodies is described, e.g., in Harrow & Lane (1988), U.S. Pat. Nos. 4,491,632, 4,472,500 and 4,444,887, and *Methods in Enzymology* 73B:3 (1981).

All publications and patents mentioned in this application are herein incorporated by reference for any purpose.

EXAMPLES

Example 1

Differentiation of Human Embryonic Stem Cells into Hepatocyte-Lineage Cells

H1-LZ-hAFP-EGFP cells are a transgenic clone derived from H1 human embryonic stem (hES) cells and carry a transgene that expresses EGFP driven by a human AFP gene promoter.

H1-LZ-hAFP-EGFP cells were cultured in medium conditioned by mitotically inactivated MEFs (CM-MEF) supplemented with 8 ng/ml bFGF (GibcoBRL/Invitrogen cat. no. 13256-029) on Matrigel-coated plates, as previously described. See, e.g., Xu et al. *Nat. Biotech.* 19:971-4 (2001). The H1-LZ-hAFP-EGFP cells were split 1 to 3 with 1 mg/ml collagenase IV (GibcoBRL/Invitrogen cat. no. 13256-029) and then fed with CM-MEF containing 8 ng/ml bFGF (GibcoBRL/Invitrogen cat. no. 13256-029) until the cells reached 90-95% confluence.

The cells were then fed with RPMI 1640 (Sigma cat. no. RS886) containing B27 supplement without vitamin A (GibcoBRL/Invitrogen cat. no. 12587-010), 1 mM sodium butyrate (Sigma Cat. no. B5887), and 100 ng/ml Activin A (R&D Systems cat. no. 338-AC-025) for one day (stage Ia). Stage Ia was designated as day 1.

On day 2, the cells were fed with RPMI 1640 containing B27 supplement without vitamin A, 0.5 mM sodium butyrate, and 100 ng/ml Activin A for two days (stage Ib).

Massive cell death was observed during stage I, and the remaining cells changed morphology to mesenchyme-like cells after two days. Some cells began to divide and formed rosette-like structures. See, e.g., FIG. 1 at panel B ("day 2").

On day 4, the cells were then fed with Knockout DMEM (GibcoBRL/Invitrogen cat. no. 10829-018) containing 20% Knockout Serum Replacement (GibcoBRL/Invitrogen cat. no. 10828-028), 2 mM l-glutamine (GibcoBRL/Invitrogen cat. no. 25030-81), 1× nonessential amino acids (GibcoBRL/Invitrogen cat. no. 11140-050), 0.1 mM β-mercaptoethanol (Sigma cat. no. M7522), and 1% DMSO (Sigma cat. no. D2650) daily for seven days (stage II).

On day 5 (one day after the cells were fed with the media for stage the cells became well-packed. See, e.g., FIG. 1 at panel C ("day 4"). The cells at day 9 are shown in FIG. 1 at panel D ("day 8").

On day 11, cells were fed with HCM Bullet Kit (Cambrex/Clonetics/Biowhittaker cat. no. CC-3198), which was supplemented with 10 ng/ml human HGF (R&D Systems cat. no.

D1756), 10 ng/ml human EGF (supplied with HCM Bullet Kit), and 1 µM dexamethasone (Sigma cat. no. D1756) daily for 10 days (stage III).

On day 15, 60-70% of the cells started to express EGFP. By day 19, hepatocyte-lineage cells showed strong EGFP expression. See, e.g., FIG. 1 at panels E and F ("HLCs day 18" and "AFP-GFP day 18").

On day 20, cells were fed with HCM Bullet Kit (Cambrex/Clonetics/Biowhittaker cat. no. CC-3198), which was supplemented with 10 ng/ml human HGF (R&D Systems cat. no. D1756), 10 ng/ml human EGF, and 25 ng/ml human oncostatin M (R&D Systems cat. no. 295-OM-050) every other day for 10 days (stage IV).

Beginning on day 25, EGFP expression gradually disappeared in that experiment. (Data not shown.)

Example 2

Liver-Specific Gene Expression and Basal p450 Isozyme Activity

At the end of each of stages Ib, II, III, and IV, total RNA was extracted from a sample of cells using a QIAGEN RNeasy Kit (cat. no. 74104). RNA from each of the stages, as well as RNA from human fetal liver (Stratagene cat. no. 738018) and RNA from human adult liver (cat. no. 735017) were analyzed by RT-PCR to determine the expression levels of the following genes: AFP; albumin; α-antitrypsin (αAT); Pregnane X receptor (PXR); p450 isoenzymes cyp2C9 (2C9), cyp3A7 (3A7), and cyp3A4 (3A4). In addition, expression of actin was analyzed as a positive control.

Figure 2:
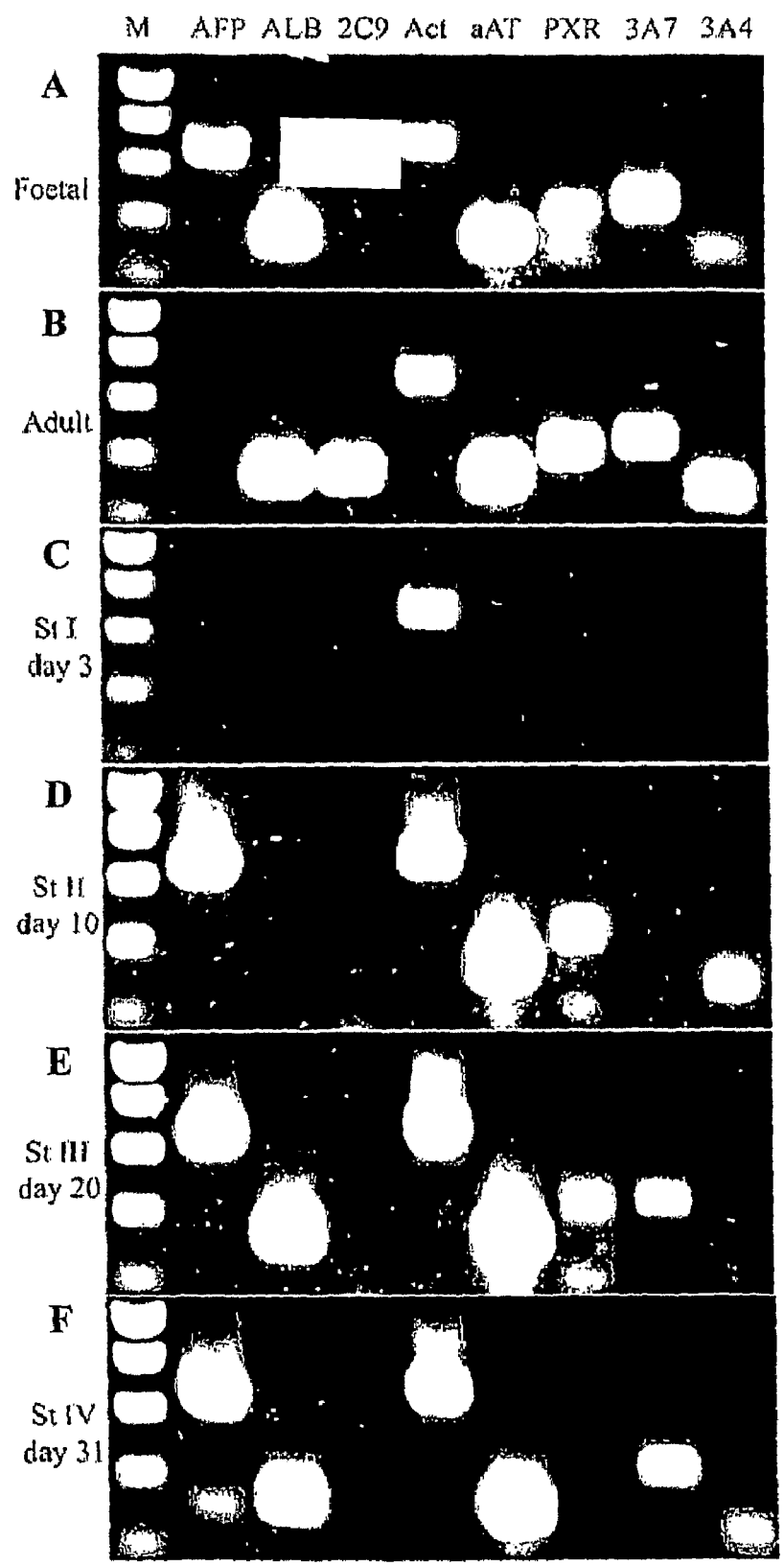
FIG. 2 shows expression of certain hepatocyte marker genes as discussed in Example 2. Panel A shows expression in fetal liver cells. Panel B shows expression in adult liver cells. Panel C shows expression at the end of stage I of the protocol described in Example 1. Panel D shows expression at the end of stage II of the protocol described in Example 1. Panel E shows expression at the end of stage III of the protocol described in Example 1. Panel F shows expression at the end of stage IV of the protocol described in Example 1.

The results of that experiment are shown in FIG. 2. Fetal and adult liver cells (panels A and B) both expressed albumin, α-antitrypsin, PXR, and p450 isoenzyme cyp3A7 at similar levels in that experiment. AFP was expressed in fetal liver cells in that experiment, but not in adult cells. p450 isoenzyme cyp2C9 was strongly expressed in adult cells, and nearly absent in fetal cells in that experiment. p450 isoenzyme cyp3A4 was also strongly expressed in adult cells, and only moderately expressed in fetal cells in that experiment.

At the end of stage I (panel C), the differentiating hES cells showed weak expression of α-antitrypsin and p450 isoenzyme cyp3A4 in that experiment. At the end of stage II (panel D), expression of α-antitrypsin and p450 isoenzyme cyp3A4 had dramatically increased in that experiment, and AFP and PXR were also robustly expressed. In addition, p450 isoenzyme cyp3A7 was weakly expressed at the end of stage II in that experiment. At the end of stage III (panel E), expression of both albumin and p450 isoenzyme cyp3A7 were significantly increased in that experiment. At the end of stage IV (panel F), p450 isoenzyme cyp2C9 was weakly expressed, and the expression of PXR had decreased in that experiment.

Example 3 p450 Isozyme Activity in Hepatocyte-Lineage Cells

Hepatocyte-lineage cells were analyzed for P450 enzyme activity using substrates phenacetin (metabolized by cyp1A2), tolbutamide (metabolized by cyp2C9), omeprazole (metabolized by cyp2C19), bufuralol (metabolized by cyp2D6) and midazolam (metabolized by cyp3A4), as follows.

Hepatocyte lineage cells differentiated as described in Example 1 were grown in four wells of a six-well plate. The medium was changed to Dulbecco's Minimum Essential Medium (Sigma-Aldrich), containing 10% foetal bovine serum (Sigma-Aldrich), 1% non-essential amino acids (Sigma-Aldrich), 2 mM glutamine (Sigma-Aldrich), 100 U/ml penicillin (Sigma-Aldrich), and 100 U/ml streptomycin (Sigma-Aldrich). HepG2 cells (ECACC no. 85011430), which exhibit a low level of constitutive activity for cyp3A4 and cyp2D6, were used as a control and grown in parallel in the same media. The HepG2 cells were seeded in 4 wells of a 6-well plate at a density of 1 million cells per well. Both the hepatocyte-lineage cells and the HepG2 cells were incubated at 37° C. in 5% $CO_2$ and air.

After 24 hours, the media was replaced with the same media, but also containing 10 µm midazolam (Ultrafine Chemicals), 10 µm bufuralol (Ultrafine Chemicals), 10 µm omeprazole (Ultrafine Chemicals), 10 µm phenacetin (Ultrafine Chemicals), and 100 µm tolbutamide (Ultrafine Chemicals). After 24 hours incubation in the presence of the substrates, the cells were harvested for a protein concentration assay and LC-MS/MS analysis.

A protein concentration assay was carried out in order to normalize the results of the LC-MS/MS analysis. The cells were rinsed twice with Dulbecco's Phosphate Buffered Saline (DPBS; Sigma-Aldrich). DPBS containing 1% Nonidet P40 (VWR) and a protease inhibitor cocktail (Roche) was added to the wells. The plates were placed on a gyro-mixer for 30 minutes at 4° C. Any cells remaining on the plates were scraped into the lysis buffer, and the buffer containing the lysed cells was transferred to a microtube. The microtube was centrifuged at 16,000×g to pellet the debris. The supernatant was then transferred to a fresh microtube and stored at −20° C.

The protein concentration assay was carried out using the method of Lowry et al. (1951) "Protein measurement with the Folin phenol reagent," *J. Biol. Chem.* 193: 265-275. Using a Microsoft Excel spreadsheet and a curve prepared from the absorbance readings of standard protein samples, the protein concentrations of the hepatocyte-lineage cells and HepG2 samples were calculated in mg/ml.

Reverse-phase HPLC with tandem mass spectrometric detection (LS-MS/MS) was used to detect the metabolites of the substrates incubated with the hepatocyte-lineage cells and HepG2 cells. 600 µl of tissue culture medium was collected from each well of the cells grown in the presence of the P450 substrates. 300 µl acetonitrile (VWR) was added to each tube and the tubes were vortexed and centrifuged at 16,000×g to pellet any debris. 300 µl aliquots from each tube were placed in a 96-well plate for LC-MS/MS analysis. Samples were stored at −70° C. prior to analysis.

A 20 µl aliquot of each sample was injected into the LC-MS/MS system, using the following conditions. The column used was Phenomenex, MercuryMS, Luna C18(2), 3 µM, 20×2.0 mm at 30° C. Solvent A was 0.1% Formic acid, and solvent B was 100% Acetonitrile. The initial flow rate was 100% Solvent A at 0.5 mL per minute. Table 4 shows the solvent percentages and flow rates through the column at various time points.

TABLE 4

| Time (min) | Solvent A (%) | Solvent B (%) | Flow Rate (mL/min) |
|---|---|---|---|
| 0 | 100 | 0 | 0.5 |
| 3 | 50 | 50 | 0.5 |
| 3.5 | 50 | 50 | 0.5 |
| 3.51 | 100 | 0 | 0.75 |
| 4.5 | 100 | 0 | 0.75 |
| 4.51 | 100 | 0 | 0.5 |

Upon exiting the column, the flow split so that approximately 250 µL per minute entered the mass spectrometer.

Using Multiple Reaction Monitoring (MRM), the positively-charged parent metabolite ions and the specific collision product ions were monitored using MassLynx 3.5. Table 5 shows the molecular weights for the parent and product ions for each metabolite, as well as the dwell time, cone voltage, collision voltage, and approximate retention time.

TABLE 5

Electrospray +ve MRM of 5 mass pairs for metabolites.

| Compound | Parent ion | Product ion | Dwell (sec) | Cone (V) | Collision (V) | Approx. Retention time (min) |
|---|---|---|---|---|---|---|
| Acetaminophen | 152.02 | 110.04 | 0.15 | 32 | 18 | 1.73 |
| 1'-hydroxybufuralol | 278.4 | 186.2 | 0.15 | 25 | 20 | 2.17 |
| 4'-hydroxytolbutamide | 287.21 | 88.9 | 0.15 | 25 | 48 | 2.90 |
| 1'-hydroxymidazolam | 342.3 | 203.2 | 0.15 | 40 | 27 | 2.70 |
| 5'-hydroxyomeprazole | 362.42 | 214.24 | 0.15 | 18 | 11 | 2.42 |

The results from the LS-MS/MS analysis were obtained as concentrations of metabolites in ng/ml. Using Microsoft Excel, the metabolism of each substrate to its metabolite was calculated in nmoles per milligram of protein, calculated using the data from the LC-MS/MS analysis of the tissue culture medium and the protein concentrations of the cell lysates from each well, discussed above.

Figure 3:
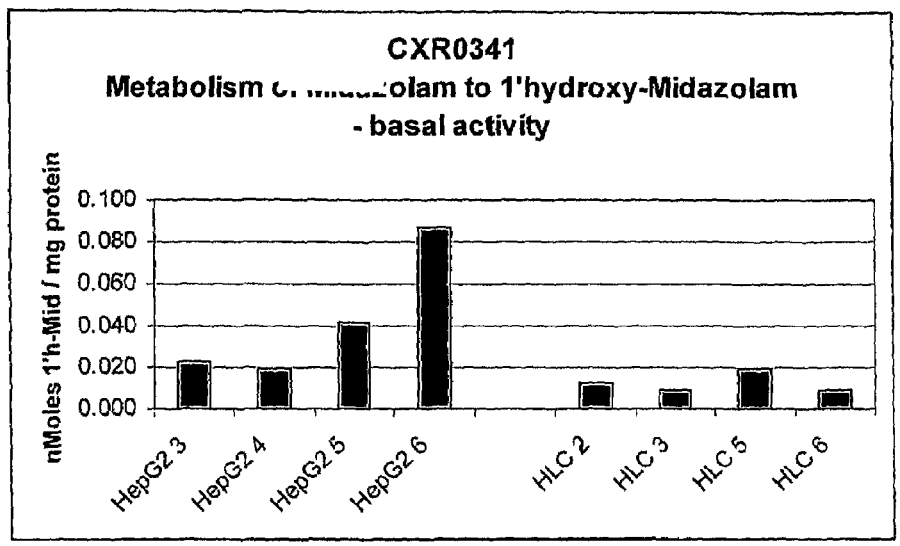
FIG. 3 shows p450 isoenzyme activity of certain hepatocyte cell lines and certain hepatocyte-lineage cells as discussed in Example 3. Panel A shows basal metabolism of midazolam. Panel B shows basal metabolism of bufuralol.
Figure 3:
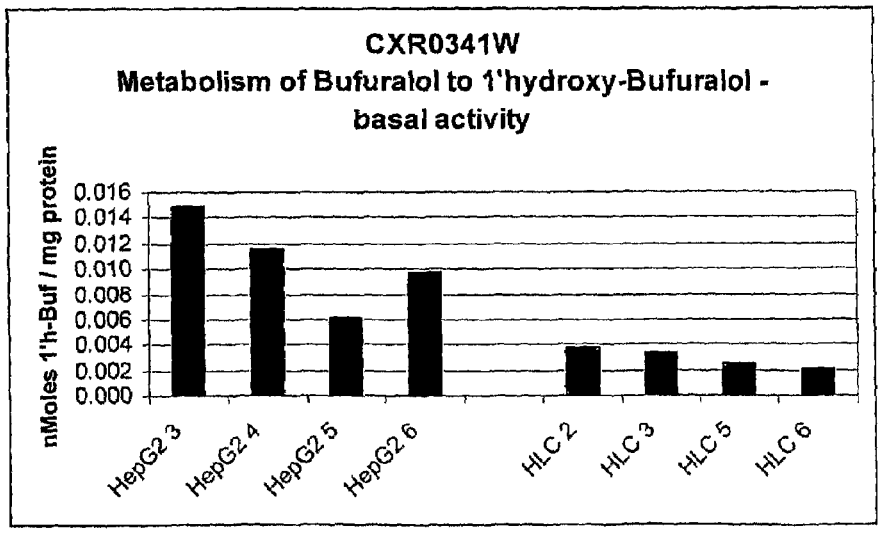

The results of that experiment are shown in FIG. 3. Metabolism of midazolam (panel A), which is metabolized by cyp3A4, and bufuralol (panel B), which is metabolized by cyp2D6, was observed in both the hepatocyte-lineage cells and HepG2 cells. No metabolism of tolbutamide, phenactin, or omeprazole was observed in the hepatocyte-lineage cells in that experiment.

Example 4

Analysis of Liver-Specific Gene Expression by Antibody Staining

Expression of certain liver-specific genes was detected by antibody staining as follows. Cells were collected after stage I, stage II, or stage III of the protocol described in Example 1. The cells were fixed and then stained with antibodies to the following liver-specific gene products: HNF4α (Santa Cruz, cat no. SC-8987), AFP (Sigma cat. no. A8452), and albumin (Sigma cat. no. A6684).

Figure 4:
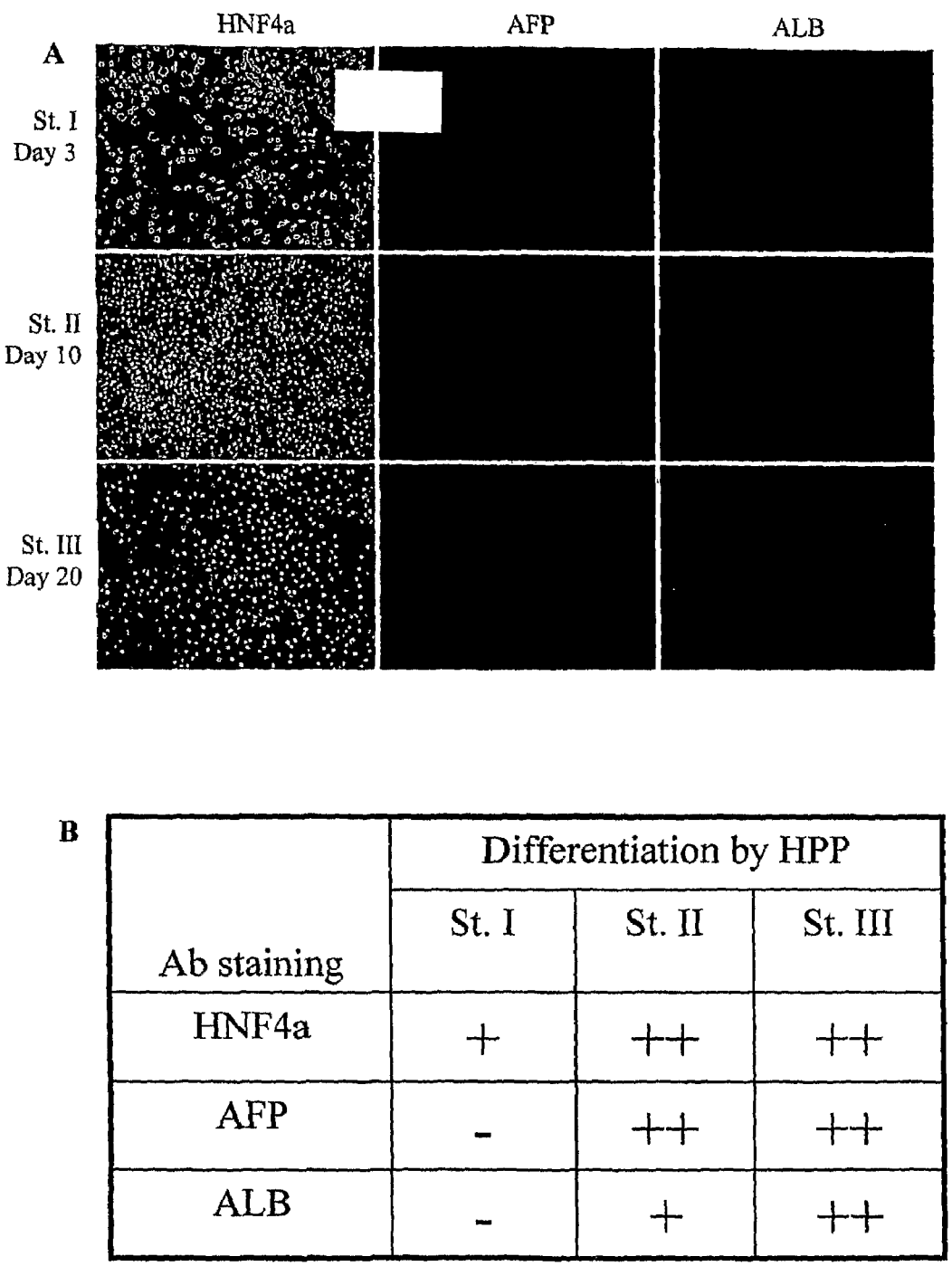
FIG. 4 shows antibody staining of cells at stage I, stage II, and stage III of the differentiation protocol described in Example 1, as discussed in Example 4. Cells were stained with antibodies to HNF4α, α-fetoprotein (AFP), and albumin (ALB). See FIG. 4A.

The results of that experiment are shown in FIG. 4. FIG. 4A shows the results of the cell staining, and FIG. 4B shows a brief summary of the data shown in FIG. 4A. Only HNF4α was detectable after stage I of the differentiation protocol. See FIG. 4, top left panel. By the end of stage II, HNF4α continued to be expressed, while AFP and albumin started to appear in the cytoplasm. See FIG. 4, middle panels. AFP expression appeared stronger than albumin expression after stage B. By the end of stage III, all three gene products were strongly expressed. See FIG. 4, bottom panels.

Example 5

Analysis of Gene Expression by RT-PCR

Expression of certain tissue-specific genes was analyzed by RT-PCR during the course of the differentiation protocol described in Example 1, and in hES cells, fetal hepatocytes, and adult hepatocytes. Specifically, expression of the following genes was analyzed: Human embryonic stem cell-specific genes hTERT, nanog, and Oct4; mesoderm-specific gene Brachyury (BRACHY); neuroectoderm-specific gene PAX6; endoderm-specific genes HEX, HNF3β, HNF4α, and GATA6; hepatocyte-specific genes AFP, TAT, APOF, TTR, and CAR; and mature hepatocyte-specific genes CYP2C9 and CYP2C19. Expression of actin was measured as a control.

Figure 5:
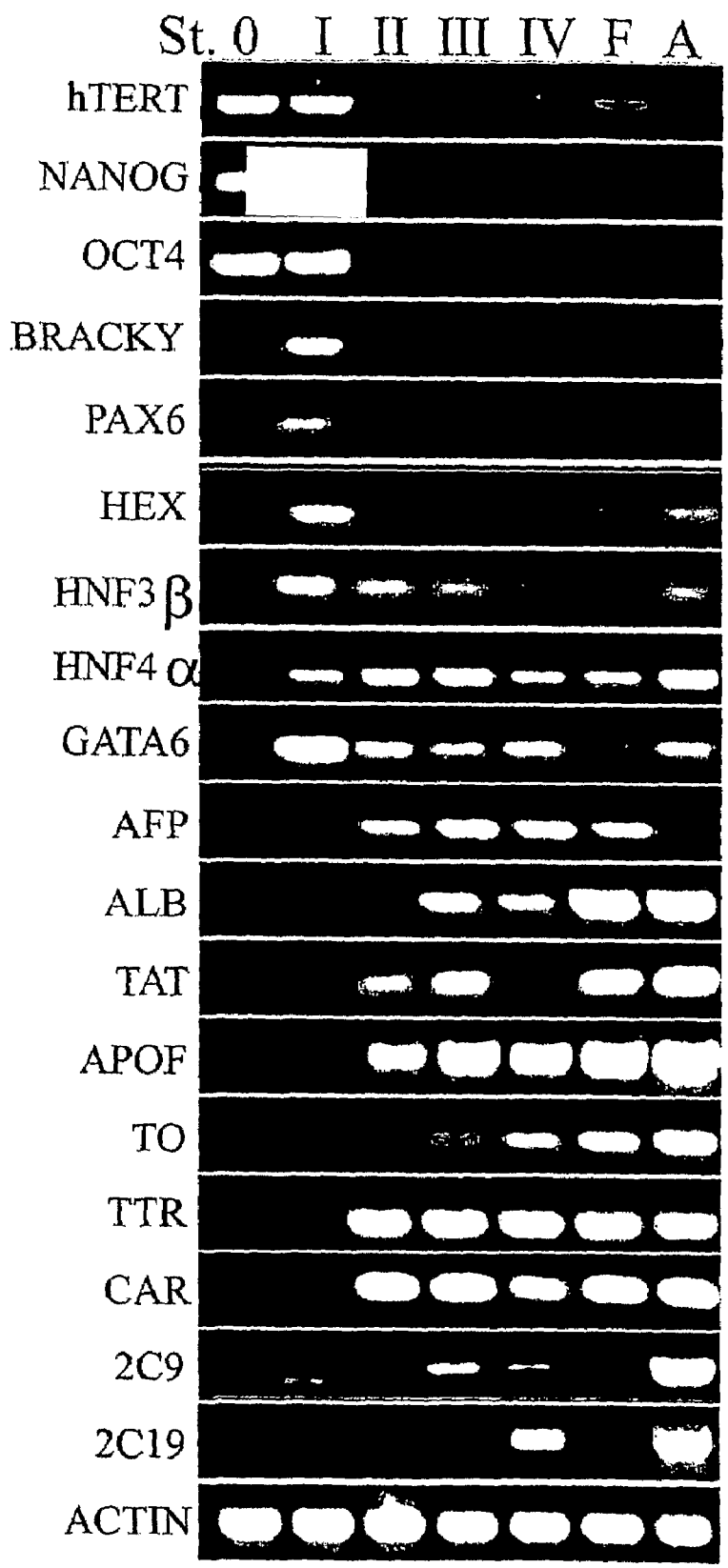
FIG. 5 shows RT-PCR analysis of various tissue-specific genes, as discussed in Example 5.

The results of that experiment are shown in FIG. 5. hES-specific genes hTERT, nanog, and Oct4 were all expressed in the hES cells and at the end of stage I. Expression of those three genes was negligible or absent in stages II through IV and in the adult hepatocyte control. A small amount of hTERT expression was observed in the fetal hepatocyte control, but expression of nanog and Oct4 was absent.

The mesoderm-specific gene BRACHY and the neuroectoderm-specific gene PAX6 were not expressed in the hES cells, but were expressed at the end of stage I. Expression of PAX6 was greatly decreased at the end of stage II, and was not detectable at the end of stage III or IV. Expression of BRACHY was not detectable at the end of stages II, III, or IV, or in fetal or adult hepatocytes. The endoderm-specific gene HEX was slightly expressed in hES cells, and more robustly expressed at the end of stage I. HEX expression was not detectable at the end of stage II, III, or IV. HEX was also slightly expressed in both fetal hepatocytes and adult hepatocytes.

Endoderm-specific transcription factors HNF3β, HNF4α, and GATA6 were all expressed from stage I through IV. Those genes were also expressed in both fetal and adult hepatocytes, but expression was undetectable or barely detectable in hES cells.

Hepatocyte-specific genes AFP, APOF, TTR, and CAR were expressed at the end of stages II, III, and IV. All of those genes were also expressed in fetal hepatocytes, and all but AFP were expressed in adult hepatocytes. Hepatocyte-specific genes albumin and TO appeared by the end of stage III and continued to be expressed through the end of stage IV. Albumin and TO were also expressed in both fetal and adult hepatocytes. Hepatocyte-specific gene TAT began to appear at the end of stage I and was expressed through the end of stage IV. TAT was also expressed in both fetal and adult hepatocytes.

Cytochrome p4-50 isoenzyme CYP2C9 was expressed at the end of stage III and at the end of stage IV, although at a slightly lower level. CYP2C9 was also expressed in adult hepatocytes, but not in fetal hepatocytes. Cytochrome p450 isoenzyme CYP2C19 was expressed at the end of stage IV and in adult hepatocytes, but not in fetal hepatocytes.

Because AFP is a fetal liver marker, while CYP2C9 and CYP2C19 are adult fetal markers, the results of this RT-PCT expression analysis suggest that the hepatocyte-lineage cells at the end of stage IV may contain a mixture of fetal and adult hepatocyte-lineage cells.

Example 6

Analysis of Glycogen Storage in Hepatocyte-Lineage Cells

Figure 6:
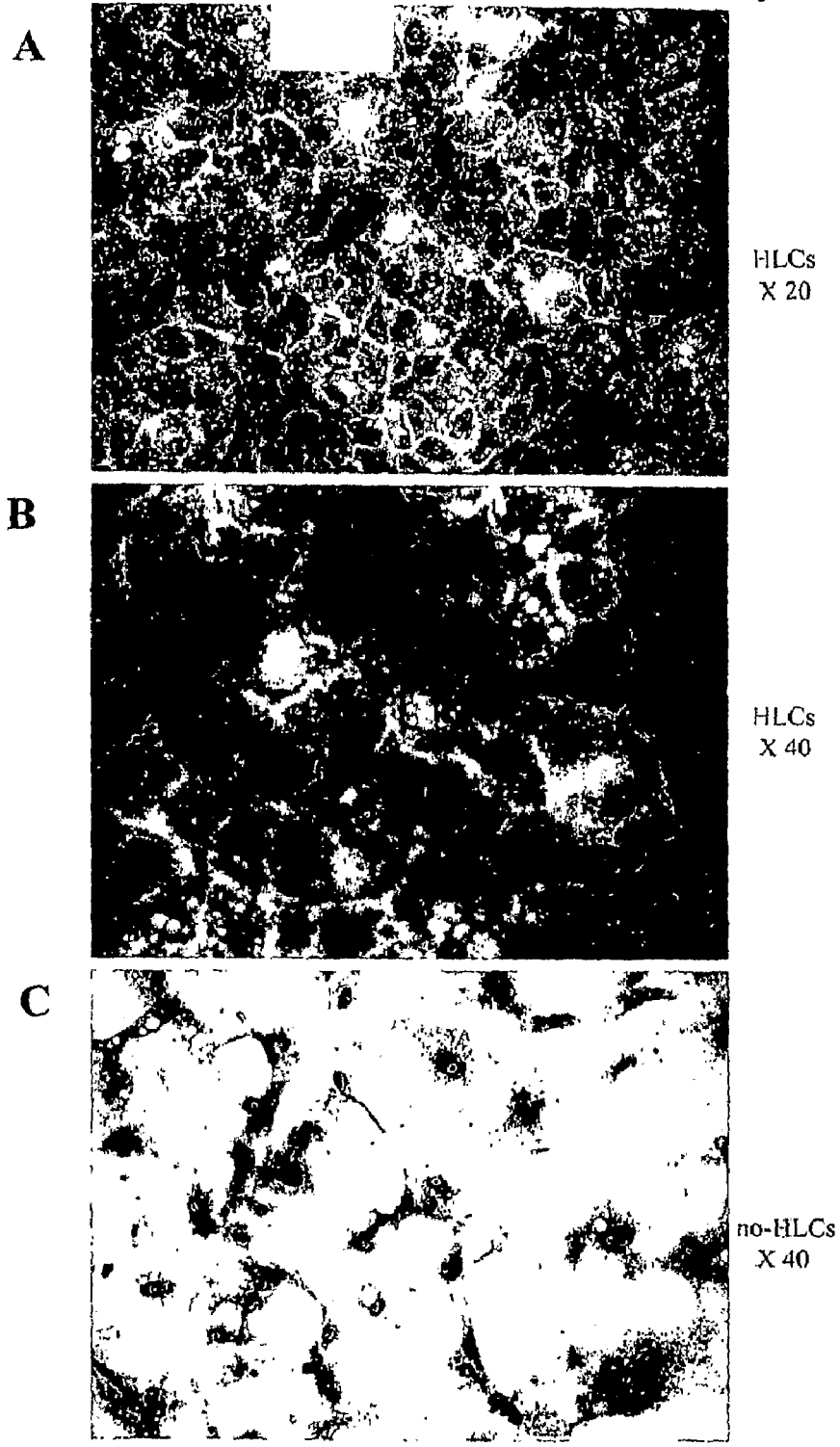
FIG. 6 shows analysis of glycogen storage by Periodic Acid Schiff staining in hepatocyte-lineage cells at two different magnifications (panels A and B) and in non-hepatocyte lineage cells (panel C), as discussed in Example 6.

Glycogen storage is a primary biological function of liver tissue. Accordingly, we analyzed glycogen storage in the hepatocyte-lineage cells derived from the differentiation protocol described in Example 1. Hepatocyte-lineage cells from day 22 of the differentiation protocol in Example 1 were stained with Periodic Acid Schiff staining agent, which reveals glycogen storage. The hepatocyte-lineage cells showed strong staining. See, e.g., FIG. 6, panels A and B. Non-hepatocyte lineage cells did not show significant staining in that assay. See FIG. 6, panel C.

Based on the glycogen storage assay results and the expression of cytochrome P450 isoenzymes discussed in Example 5, it appears that the hepatocyte-lineage cells produced by the differentiation protocol in Example 1 are not only morphologically similar to adult hepatocytes, but also have certain functions characteristic of adult hepatocytes.

Example 7

Analysis of Hepatocyte Aggregate Formation

Figure 7:
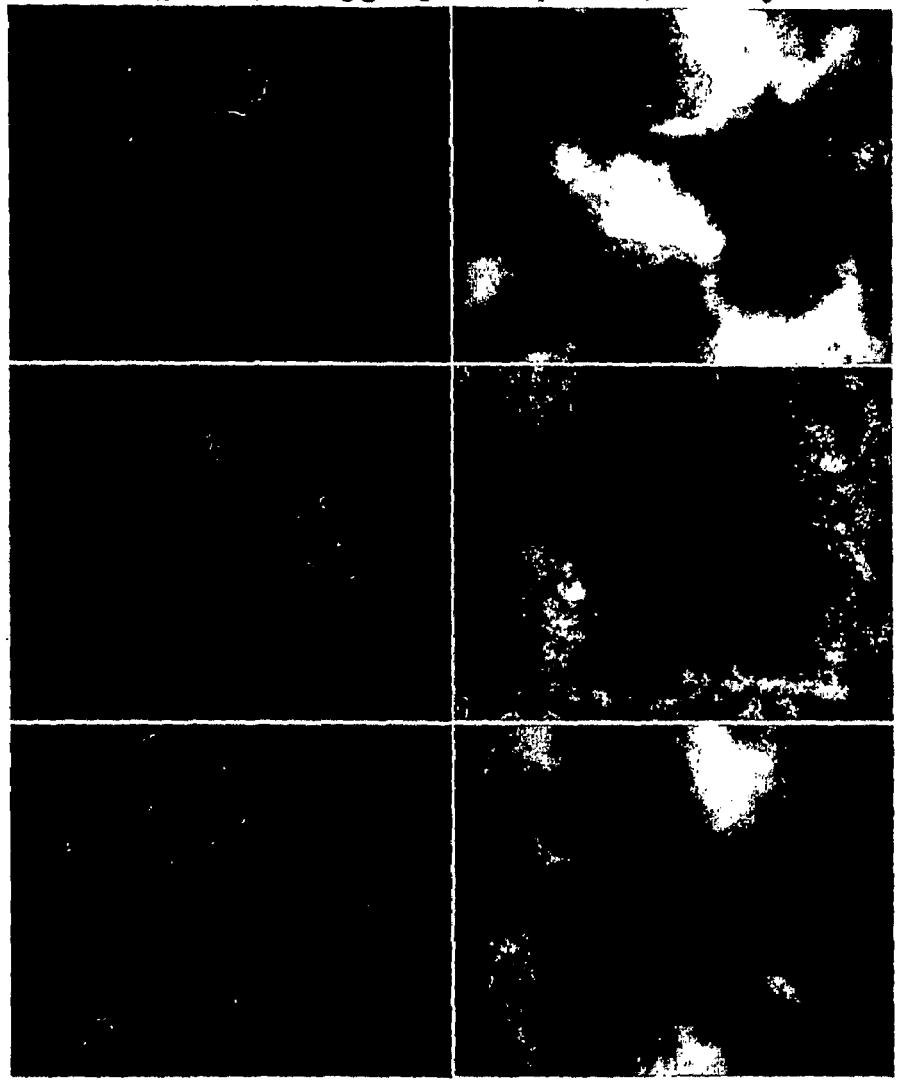
FIG. 7 shows formation of hepatocyte aggregates formed by hepatocyte-lineage cells (right panels), as discussed in Example 7. GFP expression from an hAFP-GFP construct is also shown (left panels).

Hepatocyte aggregate formation was analyzed in the hepatocyte-lineage cells produced by the protocol of Example 1. When cultured on ultra-low attachment plates, the hepatocyte-lineage cells formed aggregates. See FIG. 7, right panels. The aggregates expressed hAFP-GFP by day 14 (left panels of FIG. 7), and the hAFP-GFP signal began to disappear at day 21 (data not shown). By day 25, only very weak GFP expression was detectable (data not shown).

Example 8

Differentiation of Certain Other hES Cells into Hepatocyte-Lineage Cells

The method discussed in Example 1 was used to make hepatocyte-lineage cells from the following hES cell lines: H1 hES cells; H1-LZ-hALB-EGFP hES, which are an H1 hES cells subclone that carries a transgene that expresses EGFP driven by a human albumin promoter; and H7 hES cells. In addition, the protocol was repeated with H1-LZ-hAFP -EGFP.

Figure 8:
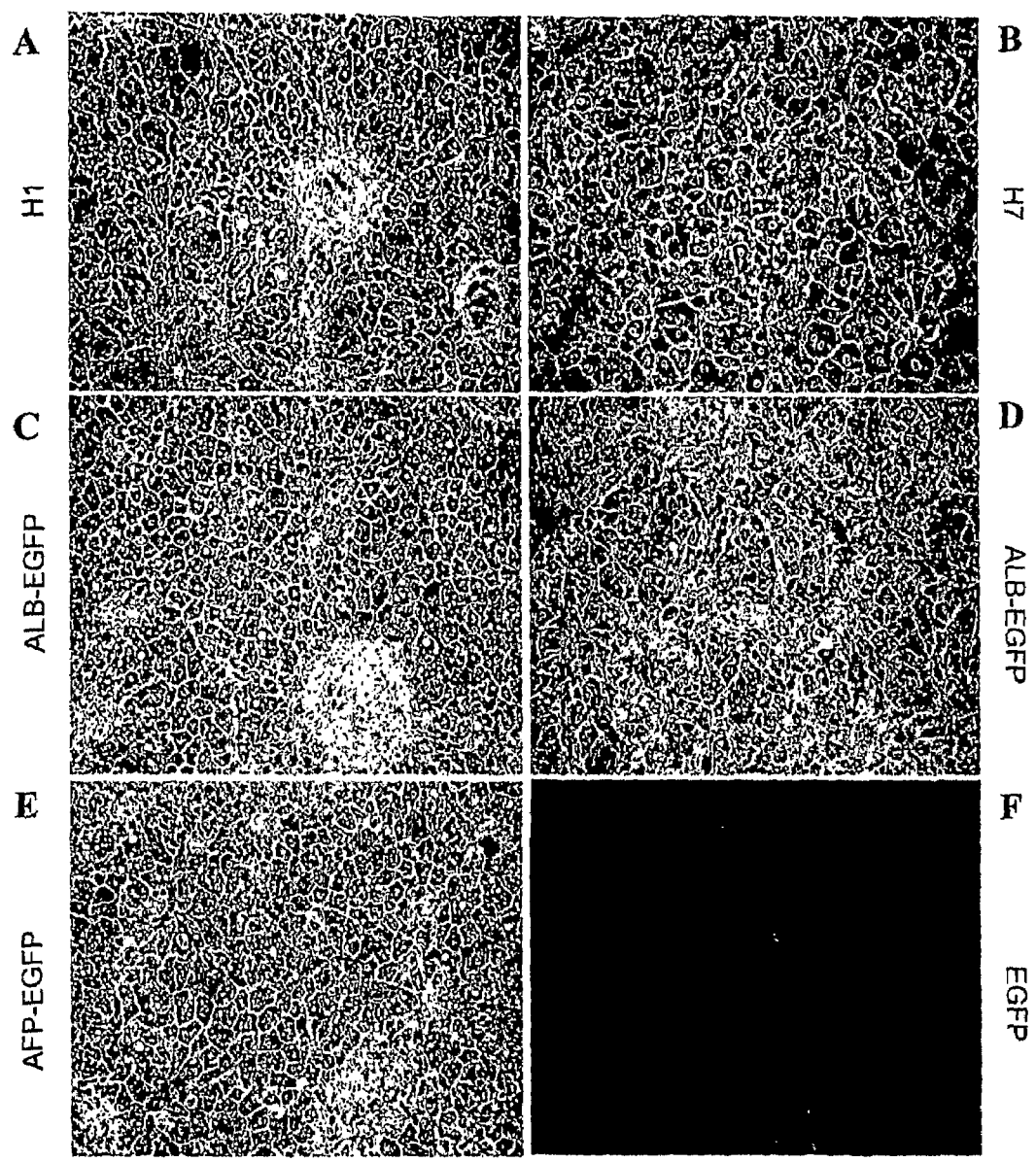
FIG. 8 shows differentiation of certain hES cell lines to hepatocyte-lineage cells at day 17 as discussed in Example 8. Panel A shows hepatocyte-lineage cells differentiated from H1 hES cells. Panel B shows hepatocyte-lineage cells differentiated from H7 hES cells. Panels C and D shows hepatocyte-lineage cells differentiated from H1-LZ-hALB-EGFP hES cells. Panels E and F show the morphology and GFP expression, respectively, in hepatocyte-lineage cells at day 18, differentiated from H1-LZ-hAFP-EGFP hES cells.

Exemplary hepatocyte-lineage cells that resulted from the differentiation protocol at day 17 are shown in FIG. 8. Both H1 hES cells and H1-LZ-hALB-EGFP hES cells produced 60-70% hepatocyte-lineage cells showing typical hepatocyte morphology in that experiment. See, e.g., FIG. 8, panels A (H1 hES cells), C (H1-LZ-hALB-EGFP hES cells), and D (H1-LZ-hALB-EGFP hES cells). H7 hES cells responded somewhat differently to the protocol, with the majority of cells dying at stage I in that experiment. The remaining cells eventually showed typical hepatocyte morphology in that experiment. See, e.g., FIG. 8, panel B. When the protocol was repeated with H1-LZ-hAFP-EGFP hES cells, 60-70% hepatocyte-lineage cells were generated in that experiment. The morphology and EGFP expression at day 17 in that experiment is shown in FIG. 8, panels E and F. H9 hES cells resulted in 60-80% of hepatocyte-lineage cells being generated (data not shown).

Example 9

Differentiation of H7p61 Human Embryonic Stem Cells into Hepatocyte-Lineage Cells Using Three-Stage Process H7p61 cells (Xu et al., *Nat. Biotech.* 19:971-974 (2001)) were cultured in medium conditioned by mitotically inactivated MEFs (CM-MEF) supplemented with 8 ng/ml bFGF (GibcoBRL/Invitrogen cat. no. 13256-029) on Matrigel-coated plates, as previously described. See, e.g., Xu et al. *Nat. Biotech.* 19:971-4 (2001). The H1-LZ-hAFP-EGFP cells were split 1 to 3 with 1 mg/ml collagenase IV (GibcoBRL/Invitrogen cat. no. 13256-029) and then fed with CM-MEF containing 8 ng/ml bFGF (GibcoBRL/Invitrogen cat. no. 13256-029) until the cells reached 90-95% confluence.

The cells were then fed with RPMI 1640 (Sigma cat. no. RS886) containing B27 supplement without vitamin A (GibcoBRL/Invitrogen cat. no. 12587-010), 1 mM sodium butyrate (Sigma Cat. no. B5887), and 100 ng/ml Activin A (R&D Systems cat. no. 338-AC-025) for one day (stage Ia). Stage Ia was designated as day 1.

On day 2, the cells were fed with RPMI 1640 containing B27 supplement without vitamin A, 0.5 mM sodium butyrate, and 100 ng/ml Activin A for two days (stage Ib). Stage 1b was designated as days 2 and 3.

Massive cell death was observed during stage I, and the remaining cells changed morphology to mesenchyme-like cells after two days. Some cells began to divide and formed rosette-like structures.

On day 4, the cells were fed with Knockout DMEM (GibcoBRL/Invitrogen cat. no. 10829-018) containing 20% Knockout Serum Replacement (GibcoBRL/Invitrogen cat. no. 10828-028), 2 mM 1-glutamine (GibcoBRL/Invitrogen cat. no. 25030-81), 1× nonessential amino acids (GibcoBRL/Invitrogen cat. no. 11140-050), 0.1 mM β-mercaptoethanol (Sigma cat. no. M7522), and 1% DMSO (Sigma cat. no. D2650) daily for seven days (stage II; days 4 to 10).

On day 11, cells were fed with modified Liebovitz L-15 media (mL 15; Sigma cat. no. L-5520) containing 8.3% (v/v) tryptose phosphate broth (Sigma cat. no. T-8159), 8.3% (v/v) heat-inactivated fetal bovine serum (FBS; Sigma cat. no. F-4135), 10 µM hydrocortisone 21-hemisuccinate (Sigma cat. no. H-4881), 1 µM bovine pancreas insulin (Sigma cat. no. I-5500), and 240 µg/ml L-glutamine (Gibco BRL cat. no. 25030-024), and supplemented with 10 ng/ml human HGF (R&D Systems cat. no. D1756) and 20 ng/ml human oncostatin M (R&D Systems cat. no. 295-OM-050) daily for 14 days (designated stage b-III, to distinguish this stage from stage III discussed in Example 1, above; days 11 to 24).

Example 10

Liver-Specific Gene Expression in Hepatocyte-Lineage Cells Differentiated from H7p61 Human Embryonic Stem Cells Using Three-Stage Process Hepatocyte-lineage cells differentiated from H7p61 ES cells as described in Example 9 were analyzed for expression of certain liver-specific genes. On each of days 1 through 17, and on days 21 and 24, total RNA was extracted from a sample of cells using a QIAGEN RNeasy Kit (cat. no. 74104).

Figure 9:
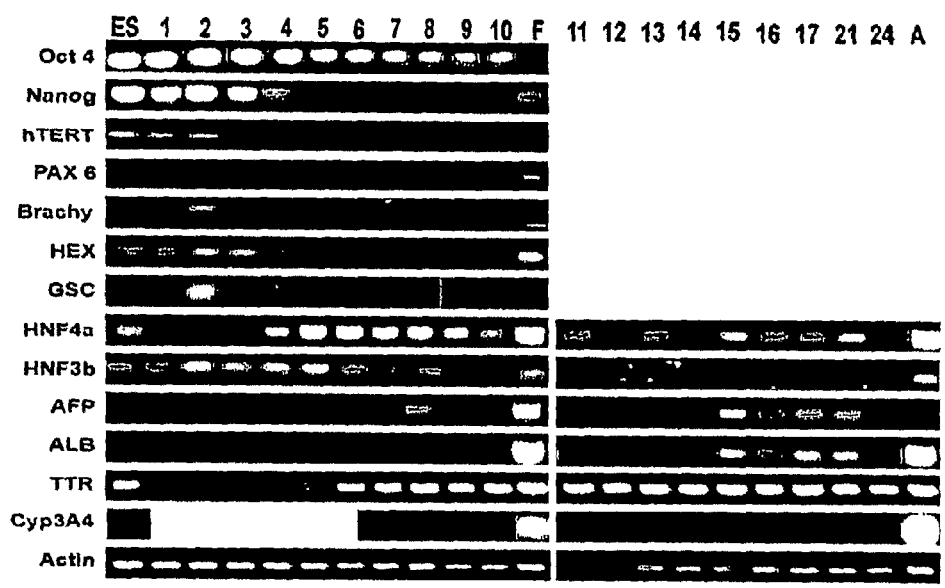
FIG. 9 shows expression of certain hepatocyte marker genes during differentiation of H7p61 hES cells to hepatocyte-lineage cells, as discussed in Examples 9 and 10.

RNA from cells from each of the days, as well as RNA from H7p61 ES cells, human fetal liver (lane "F" in FIG. 9; Stratagene cat. no. 738018), and human adult liver (lane "A" in FIG. 9; Stratagene cat. no. 735017) were analyzed by RT-PCR to determine the expression levels of the following genes: endoderm-specific genes HNF4α and HNF3β; hepatocyte-specific genes AFP, albumin, and TTR. Expression of p450 isoenzyme cyp3A4 was analyzed by RT-PCR in H7p61 ES cells, from days 7 through 17, 21, and 24, and in fetal and adult liver cells. RNA from H7p61 ES cells, from days 1 through 10, and from fetal liver was analysed by RT-PCR to determine the expression levels of the following genes: Human embryonic stem cell-specific genes Oct4, nanog, and hTERT; neuroectoderm-specific gene PAX6; mesoderm-specific gene Brachyury (Brachy); endoderm-specific genes HEX and goosecoid (GSC). Finally, expression of actin was analyzed as a positive control for all samples.

The results of that experiment are shown in FIG. 9. In that experiment, the hepatocyte-lineage cells differentiated from H7p61 ES cells expressed HNF4α, HNF3β, albumin, and TTR, as did adult liver cells (A). The hepatocyte-lineage cells also expressed p450 isoenzyme cyp3A4 in that experiment.

Example 11

Liver-Specific Gene Expression in Hepatocyte-Lineage Cells Differentiated from H7p72 Human Embryonic Stem Cells Using Three-Stage Process Hepatocyte-lineage cells were differentiated from H7p72 ES cells (Xu et al., Nat. Biotech. 19: 971-974 (2001)) by the method described in Example 9, above. The hepatocyte-lineage cells were then analyzed for expression of certain liver-specific genes. On days 1, 2, 3, 5, 7, 9, 11, 13, 15, 17, and 21 of the protocol, total RNA was extracted from a sample of cells using a QIAGEN RNeasy Kit (cat. no. 74104). RNA from cells from each of the days, as well as RNA from H7p72 ES cells, human fetal liver (late "F" in FIG. 10; Stratagene cat. no. 738018), and human adult liver (lane "A" in FIG. 10; Stratagene cat. no. 735017) was analyzed by RT-PCR to determine the expression levels of the following genes: Human embryonic stem cell-specific genes Oct4, nanog, and hTERT; neuroectoderm-specific gene PAX6; mesoderm-specific gene Brachyury (Brachy); endoderm-specific genes GATA4, GATA6, HEX, GSC, HNF4α, and HNF3β; hepatocyte-specific genes AFP, albumin, TO, TTR, TAT, ApoF, CAR, and PXR1; and mature hepatocyte-specific genes P450 isoenzymes Cyp3A4, Cyp3A7, Cyp2C9, and Cyp2C19. Expression of actin was analyzed as a positive control for all samples.

Figure 10:
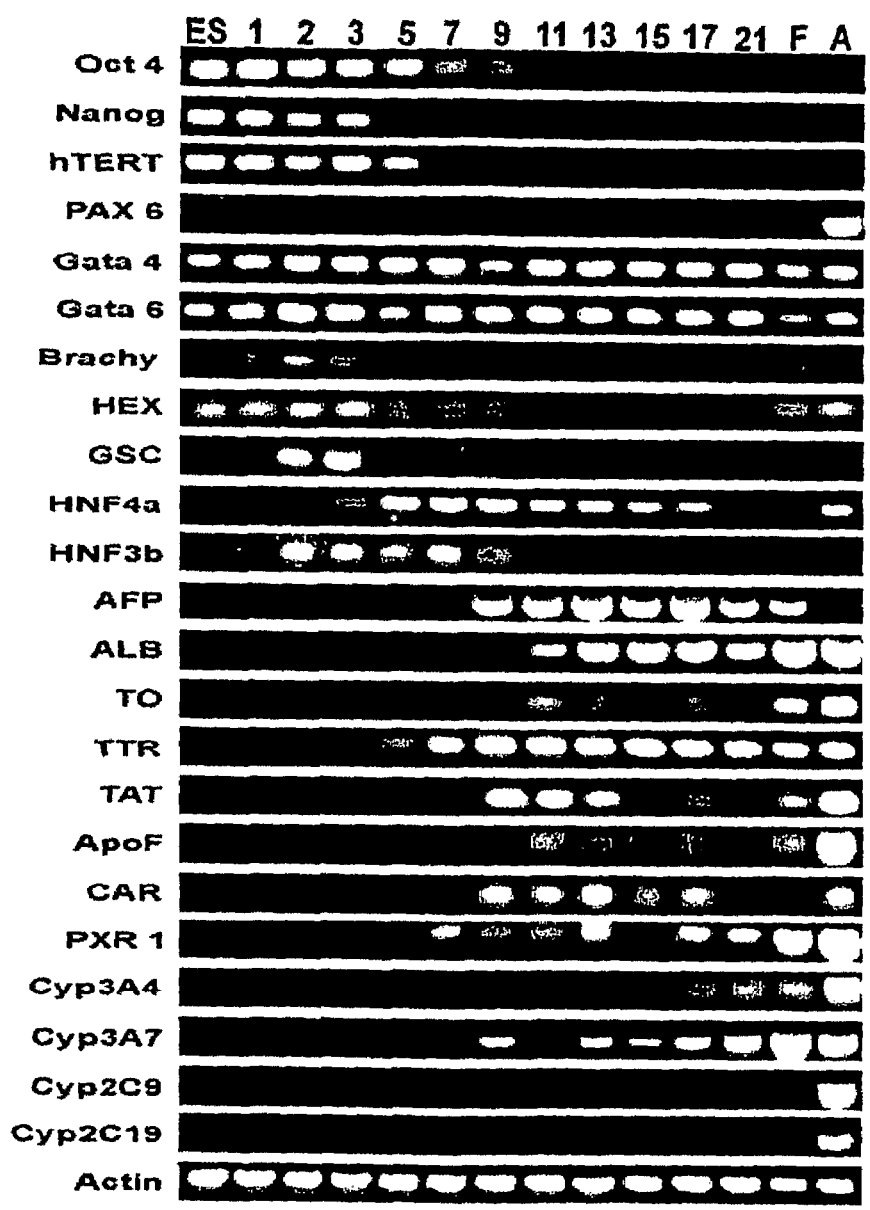
FIG. 10 shows expression of certain hepatocyte marker genes during differentiation of H7p72 hES cells to hepatocyte-lineage cells, as discussed in Example 11.

The results of that experiment are shown in FIG. 10. In that experiment, the hepatocyte-lineage cells differentiated from H7p72 ES cells expressed HNF4α, HNF3β, albumin, TO, TTR, TAT, ApoF, CAR, PXR1, and P450 isoenzymes Cyp3A4 and Cyp3A7, as did adult liver cells (A).

Example 12

Differentiation of H1p53 Human Embryonic Stem Cells into Hepatocyte-Lineage Cells Using Three-Stage Process H1p53 cells (Xu et al., Nat. Biotech. 19:971-974 (2001)) were cultured in medium conditioned by mitotically inactivated MEFs (CM-MEF) supplemented with 8 ng/ml bFGF (GibcoBRL/Invitrogen cat. no. 13256-029) on Matrigel-coated plates, as previously described. See, e.g., Xu et al. Nat. Biotech. 19:971-4 (2001). The H1-LZ-hAFP-EGFP cells were split 1 to 3 with 1 mg/ml collagenase IV (GibcoBRL/Invitrogen cat. no. 13256-029) and then fed with CM-MEF containing 8 ng/ml bFGF (GibcoBRL/Invitrogen cat. no. 13256-029) until the cells reached 90-95% confluence.

The cells were then fed with RPMI 1640 (Sigma cat. no. RS886) containing B27 supplement without vitamin A (GibcoBRL/Invitrogen cat. no. 12587-010), 1 mM sodium butyrate (Sigma Cat. no. B5887), and 100 ng/ml Activin A (R&D Systems cat. no. 338-AC-025) for two days (stage Ia). Stage Ia was designated as day 1 in order to make the differentiation method easily comparable to the methods of Examples 9 and 11.

On day 3, the cells were fed with RPMI 1640 containing B27 supplement without vitamin A, 0.5 mM sodium butyrate, and 100 ng/ml Activin A for three days (stage Ib). Stage 1b was designated as days 2 and 3 in order to make the differentiation method easily comparable to the methods of Examples 9 and 11.

Massive cell death was observed during stage I, and the remaining cells changed morphology to mesenchyme-like cells after two days. Some cells began to divide and formed rosette-like structures.

On day 6, the cells were fed with Knockout DMEM (GibcoBRL/Invitrogen cat. no. 10829-018) containing 20% Knockout Serum Replacement (GibcoBRL/Invitrogen cat. no. 10828-028), 2 mM 1-glutamine (GibcoBRL/Invitrogen cat. no. 25030-81), 1× nonessential amino acids (GibcoBRL/Invitrogen cat. no. 11140-050), 0.1 mM β-mercaptoethanol (Sigma cat. no. M7522), and 1% DMSO (Sigma cat. no. D2650) daily for seven days (stage II; designated days 4 to 10).

One day after the cells were fed with the media for stage II, the cells became well-packed.

On day 13, cells were fed with modified Liebovitz L-15 media (mL 15; Sigma cat. no. L-5520) containing 8.3% (v/v) tryptose phosphate broth (Sigma cat. no. T-8159), 8.3% (v/v) heat-inactivated fetal bovine serum (FBS; Sigma cat. no. F-4135), 10 μM hydrocortisone 21-hemisuccinate (Sigma cat. no. H-4881), 1 μM bovine pancreas insulin (Sigma cat. no. I-5500), and 240 μg/ml L-glutamine (Gibco BRL cat. no. 25030-024), and supplemented with 10 ng/ml human HGF (R&D Systems cat. no. D1756) and 20 ng/ml human oncostatin M (R&D Systems cat. no. 295-OM-050) daily for 14 days (designated stage b-III, to distinguish this stage from stage III discussed in Example 1, above; designated days 11 to 24).

Example 13

Liver-Specific Gene Expression in Hepatocyte-Lineage Cells Differentiated from H1p53 Human Embryonic Stem Cells Using Three-Stage Process Hepatocyte-lineage cells differentiated from H1p53 ES cells as described in Example 12 were analyzed for expression of certain liver-specific genes. On days 1, 2, 3, 5, 7, 9, 11, 13, 15, 17, 19, 21, and 24 of the protocol, total RNA was extracted from a sample of cells using a QIAGEN RNeasy Kit (cat. no. 74104). RNA from cells from each of the days, as well as RNA from H1p53 ES cells, human fetal liver (lane "F" in FIG. 11; Stratagene cat. no. 738018), and human adult liver (lane "A" in FIG. 11; Stratagene cat. no. 735017) was analyzed by RT-PCR to determine the expression levels of the following genes: Human embryonic stem cell-specific genes Oct4, nanog, and hTERT; neuroectoderm-specific gene PAX6; mesoderm-specific gene Brachyury (Brachy); endoderm-specific genes GATA4, GATA6, HEX, GSC, HNF4α, and HNF3β; hepatocyte-specific genes AFP, albumin TO, TTR, TAT, ApoF, CAR, and PXR1; and mature hepatocyte-specific genes P450 isoenzymes Cyp3A4, Cyp3A7, Cyp2C9, and Cyp2C19. Expression of actin was analyzed as a positive control for all samples.

Figure 11:
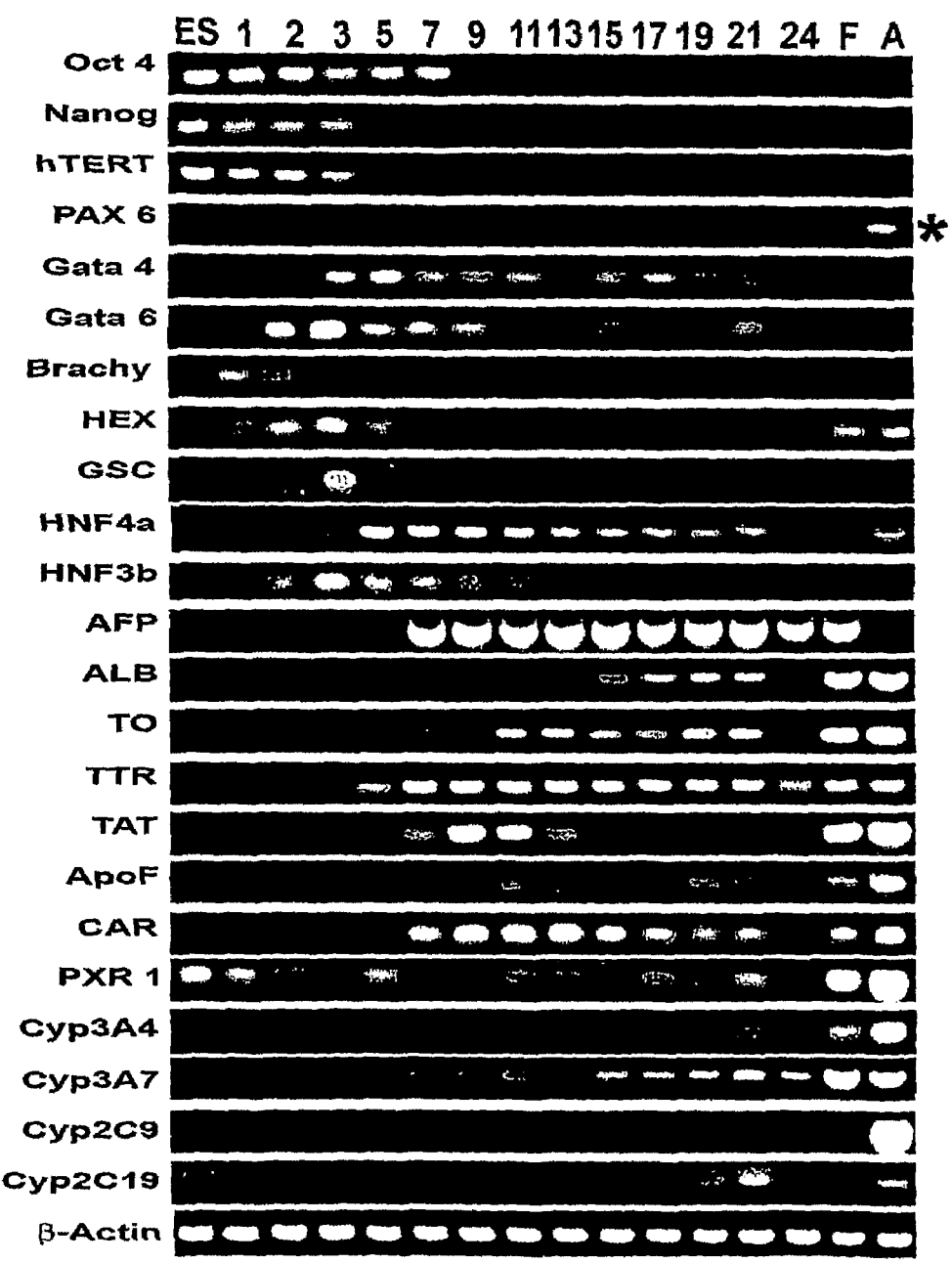
FIG. 11 shows expression of certain hepatocyte marker genes during differentiation of H1p53 hES cells to hepatocyte-lineage cells, as discussed in Examples 12 and 13.

The results of that experiment are shown in FIG. 11. In that experiment, the hepatocyte-lineage cells differentiated from H1p53 ES cells expressed HNF4α, HNF3β, albumin, TO, TTR, TAT, CAR, PXR1, and P450 isoenzymes Cyp3A4, Cyp3A7, and Cyp2C19, as did adult liver cells (A). The control RNA for PAX6 in that experiment, indicated by an asterisk in FIG. 11, was not from fetal or adult liver cells, but from a neural differentiation protocol.

Example 14

Liver-Specific Protein Expression in Hepatocyte-Lineage Cells Differentiated from H7p72 and H1p53 Human Embryonic Stem Cells Using Three-Stage Process Hepatocyte-lineage cells differentiated from H7p72 ES cells as described in Example 11 (referring to Example 9) and hepatocyte-lineage cells differentiated from H1p53 ES cells as described in Example 12 were analyzed for protein expression of certain liver-specific proteins. On days 0 (i.e., undifferentiated ES cells), 1, 2, 3, 5, 7, 9, 11, 13, 15, 17, and 21 of the protocol, cells were lysed in 300 μl of 1× boiling mix (0.5 ml β-mercaptoethanol, 1 ml glycerol, 1 ml Spacer gel buffer [5.1 g Tris base and 0.4 g SDS, to a final volume of 100 ml with distilled $H_2O$, and to a pH of 6.7 with HCl], 0.8 nil of 25% SDS, 0.05% bromophenol blue, 6.6 mls distilled water) with heating to 80° C. for 5 minutes. The lysates were then separated on a 10% SDS-PAGE gel. Expression of the following proteins was detected by standard Western blotting procedures using antibodies to the following proteins (sources for the antibodies shown in parentheses): albumin (Sigma), AAT (QED Bioscience), AFP (Sigma), Sox17 (a marker for definitive endoderm; Santa Cruz), Sox7 (a marker for embryonic endoderm; Santa Cruz), HNF3β (R&D Systems), HNF4α (Santa Cruz), P450 isoenzyme Cyp3A4 (CXR Biosciences), c-Met (an HGF receptor; Santa Cruz), Oct4 (Santa Cruz), GSC (Santa Cruz), E-Cad (an epithelial cell marker; Dako), and P450R (involved in activation of P450 isoenzymes; R&D Systems). Actin (Sigma) was detected as a positive control for all samples.

Figure 12:
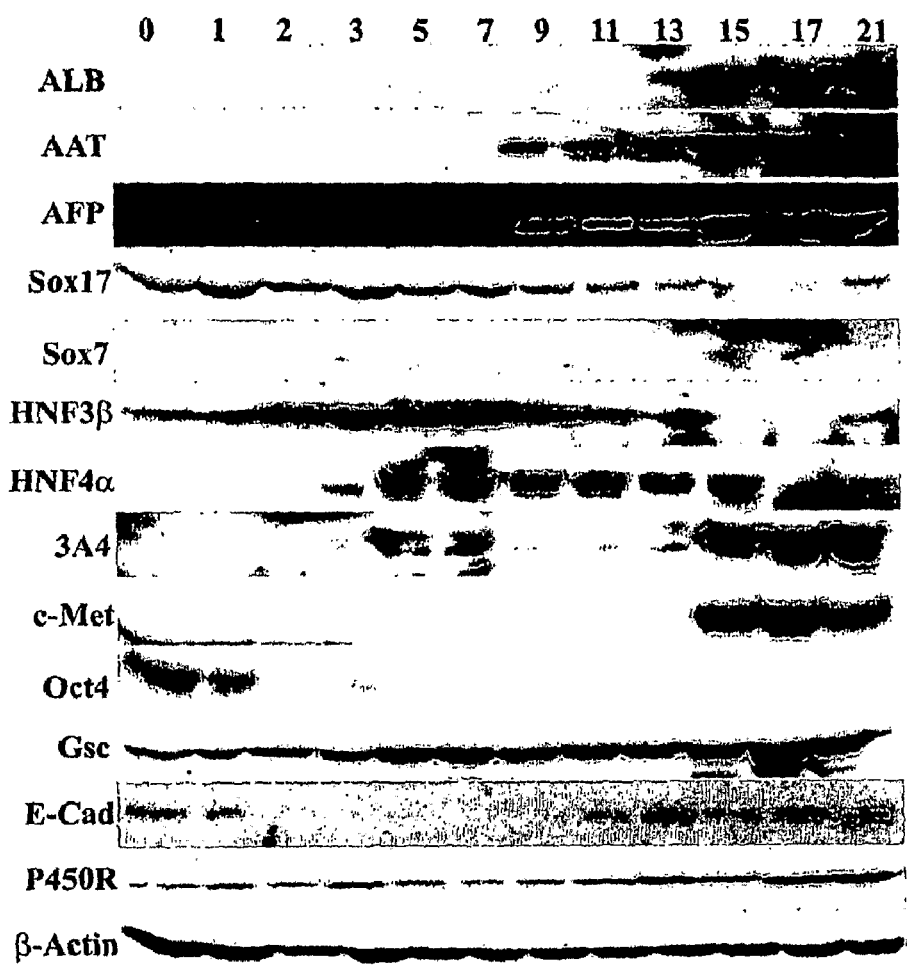
FIG. 12 shows expression of certain hepatocyte marker proteins during differentiation of H7p72 hES cells to hepatocyte-lineage cells, as discussed in Example 14.
Figure 13:
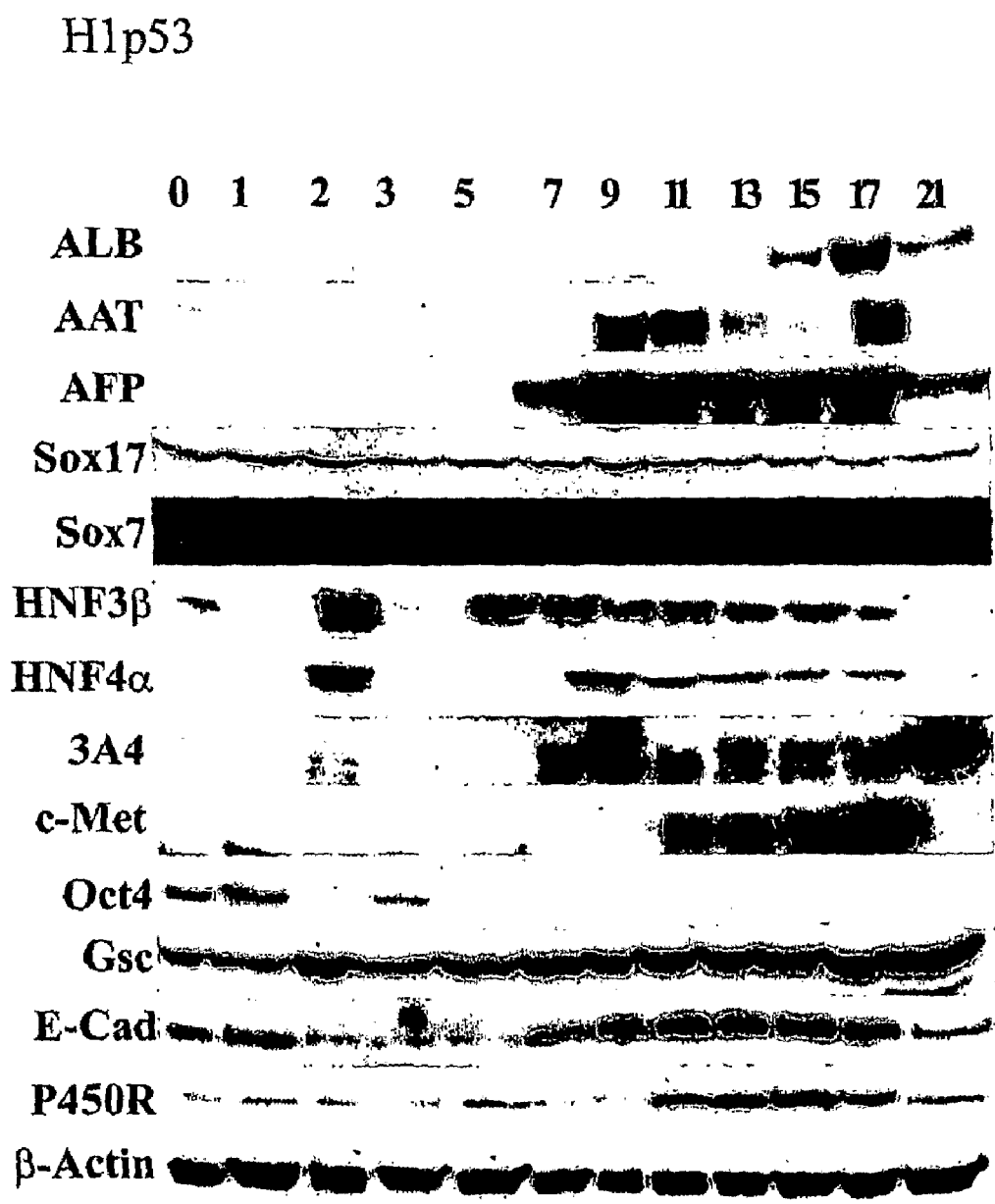
FIG. 13 shows expression of certain hepatocyte marker proteins during differentiation of H1p53 hES cells to hepatocyte-lineage cells, as discussed in Example 14.

The results of those experiments are shown in FIG. 12 (differentiation from H7p72 ES cells) and FIG. 13 (differentiation from H1p53 ES cells). In those experiments, the hepatocyte-lineage cells differentiated from either H7p72 ES cells or from H1p53 ES cells expressed albumin, AAT; HNF3β, HNF4α, P450 isoenzyme Cyp3A4, c-Met, Gsc, E-Cad, and P450R, which are characteristic of hepatocytes.

Example 15

Protein Secretion from Hepatocyte-Lineage Cells Differentiated from H7p61 Human Embryonic Stem Cells Using Three-Stage Process To test the functionality of the hepatocyte-lineage cells differentiated from H7p61 ES cells as described in Example 9, the production and export of certain plasma proteins important in maintaining homeostasis of the body were measured. Such plasma proteins include fibrinogen, a zymogen of fibrin that is involved in blood clotting; fibronectin, an extracellular protein that binds certain receptor proteins; and alpha-2 macroglobulin (A2M), a multifunctional binding protein.

Hepatocyte-lineage cells differentiated from H7p61 ES cells as described in Example 9 were analyzed for protein secretion by ELISA as follows. Cell supernatants were collected on day 0 and each of days 11 through 21 for the protein secretion assay. Secreted hepatic proteins alpha-2-macroglobulin (A2M), haptoglobin, fibrinogen, and fibronectin were analyzed using sandwich enzyme-linked immunosorbent assays (ELISA) essentially as described by the manufacturer (DAKO, Ely, UK). In addition, secretion of pre-albumin, AFP, and α-1-antichymotrypsin (a-1-ACT) was also analyzed.

High-binding EIA plates (Corning, Koolhovenlann, Netherlands) were coated overnight at 4° C. with a rabbit anti-human antibody (DAKO, Ely, UK) to each specific protein. Antibodies to A2M and fibronectin were diluted 1:1000, antibodies to haptoglobin were diluted 1:2000, and antibodies to fibrinogen were diluted 1:10,000. Sample supernatants were diluted 1:10 and then added to the EIA plates in triplicate. The plates were incubated for 2 hours at room temperature. Peroxidase-conjugated rabbit anti-human antibodies to the appropriate protein (all from Dako) were added to the plates, and the plates were incubated for 1 hour at room temperature. The substrate o-phenylenediamine (OPD) was then added to the plates and the reactions stopped with 0.5M sulphuric acid. The plates were read at 490 nm with a reference wavelength of 630 nm using a MRX II plate reader (Dynatech, Billinghurst, UK). The concentration of the appropriate protein in each sample was calculated from standard curves using the MRX II Endpoint software. Analysis of significance between variables was performed using the paired two-tailed t-test. A difference was considered significant using 95% confidence intervals ($P<0.05$).

Figure 14:
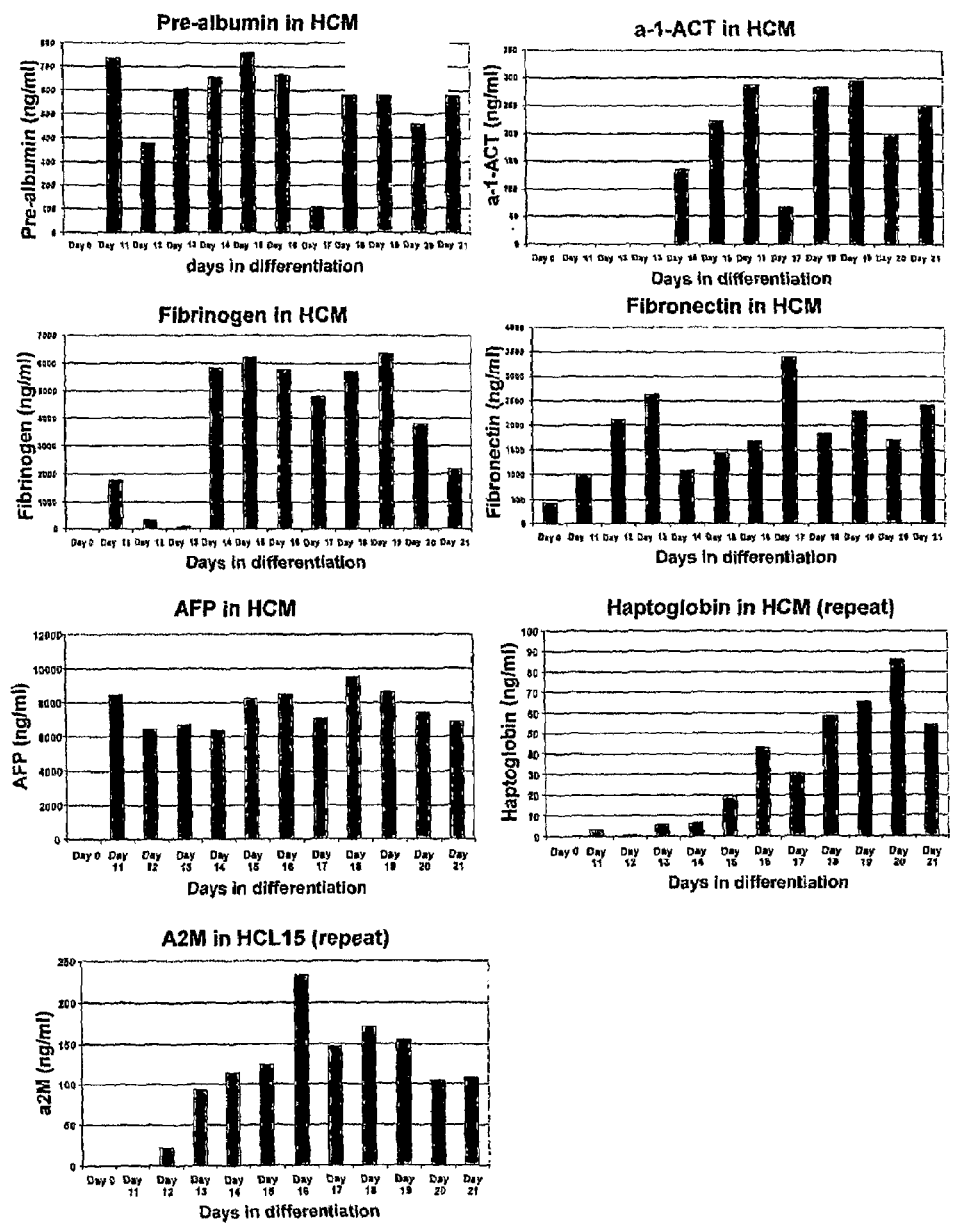
FIG. 14 shows secretion of certain hepatocyte marker proteins during differentiation of H7p61 cells to hepatocyte-lineage cells, as discussed in Example 15.

The results of that experiment are shown in FIG. 14. Secretion of hepatic proteins alpha-2-macroglobulin (A2M), haptoglobin, fibrinogen, pre-albumin, α-1-antichymotrypsin (a-1-ACT), and fibronectin increased significantly during the differentiation protocol in that experiment, indicating that the hES-cell derived hepatocyte-lineage cells were becoming more mature. Secretion of AFP remained steady during the differentiation protocol in that experiment.

Example 16

Protein Secretion from Hepatocyte-Lineage Cells Differentiated from H1p53 Human Embryonic Stem Cells Using Three-Stage Process Hepatocyte-lineage cells differentiated from H1p53 ES cells as described in Example 12 were analyzed for protein secretion by ELISA as described in Example 15, above. On each of days 1 through 14, cell supernatants were analyzed for secreted hepatic proteins alpha-2-macroglobulin (A2M), haptoglobin, fibrinogen, and fibronectin using sandwich enzyme-linked immunosorbent assays (ELISA) essentially as described by the manufacturer (DAKO, Ely, UK). In addition, secretion of pre-albumin and AFP was also analyzed. (Data not shown.)

In agreement with the results discussed in Example 15, secretion of hepatic proteins alpha-2-macroglobulin (A2M), haptoglobin, fibrinogen, pre-albumin, and fibronectin increased significantly during the differentiation protocol in that experiment, indicating that the hES-cell derived hepatocyte-lineage cells were becoming more mature. Secretion of AFP remained steady during the differentiation protocol in that experiment.

We claim:

1. A method of obtaining hepatocyte-lineage cells comprising sequentially culturing primate pluripotent stem cells in the following order:
   culturing in a first culture medium comprising an Activin;
   culturing in a second culture medium comprising at least one of an HGF polypeptide, an EGF polypeptide, and an OSM polypeptide; and
   determining that the resultant population of cells contains at least 40% hepatocyte-lineage cells.

2. The method of claim 1, wherein the primate pluripotent stem cells are human embryonic stem cells.

3. The method of claim 1, wherein the Activin comprises an Activin peptide.

4. The method of claim 3, wherein the Activin peptide comprises an active fragment of at least one of Activin A, Activin B, and Activin C.

5. The method of claim 1, wherein the Activin comprises at least one of Activin A, Activin B, and Activin C.

6. The method of claim 5, wherein the Activin is Activin A.

7. The method of claim 1, wherein the HGF polypeptide is an active fragment of an HGF.

8. The method of claim 1, wherein the HGF polypeptide is an HGF.

9. The method of claim 1, wherein the EGF polypeptide is an active fragment of an EGF.

10. The method of claim 1, wherein the EGF polypeptide is an EGF.

11. The method of claim 1, wherein the OSM polypeptide is an active fragment of an OSM.

12. The method of claim 1, wherein the OSM polypeptide is an OSM.

13. The method of claim 1, wherein the first culture medium further comprises sodium butyrate.

14. The method of claim 1, further comprising a step after step (a) and before step (b), comprising culturing in a third culture medium comprising DMSO.

15. The method of claim 1, wherein the second culture medium comprises an HGF polypeptide and an EGF polypeptide.

16. The method of claim 15, wherein the second culture medium further comprises dexamethasone.

17. The method of claim 15, further comprising a step after step (b), comprising culturing in a fourth culture medium comprising an HGF polypeptide, an EGF polypeptide, and an OSM polypeptide.

18. The method of claim 1, comprising characterizing the resultant population of cells as containing at least 60% hepatocyte-lineage cells.

19. The method of claim 1, comprising characterizing the resultant population of cells as containing at least 80% hepatocyte-lineage cells.

20. The method of claim 1, comprising characterizing the resultant population of cells as containing at least 90% hepatocyte-lineage cells.

21. A method of obtaining hepatocyte-lineage cells comprising sequentially culturing primate pluripotent stem cells in the following order:
   culturing in a first culture medium comprising an Activin and sodium butyrate;
   culturing in a second culture medium comprising DMSO;
   culturing in a third culture medium comprising an HGF polypeptide, an EGF polypeptide, and dexamethasone;
   culturing in a fourth culture medium comprising an HGF polypeptide, an EGF polypeptide, and an OSM polypeptide.

22. The method of claim 21, further comprising a step after step (a) and before step (b) comprising culturing in a fifth culture medium comprising Activin and sodium butyrate, wherein the concentration of at least one of Activin and sodium butyrate is different than the concentration of the same factor in step (a).

* * * * *